US010869626B2

(12) United States Patent
Krupat et al.

(10) Patent No.: US 10,869,626 B2
(45) Date of Patent: Dec. 22, 2020

(54) IMAGE ANALYSIS FOR EMOTIONAL METRIC EVALUATION

(71) Applicant: Affectiva, Inc., Boston, MA (US)

(72) Inventors: Jason Krupat, Needham, MA (US); Rana el Kaliouby, Milton, MA (US); Jason Radice, Sharon, NH (US); Chilton Lyons Cabot, Dedham, MA (US)

(73) Assignee: Affectiva, Inc., Boston, MA (US)

( * ) Notice: Subject to any disclaimer, the term of this patent is extended or adjusted under 35 U.S.C. 154(b) by 98 days.

(21) Appl. No.: 16/017,037

(22) Filed: Jun. 25, 2018

(65) Prior Publication Data

US 2018/0303397 A1     Oct. 25, 2018

Related U.S. Application Data

(63) Continuation-in-part of application No. 14/328,554, filed on Jul. 10, 2014, now Pat. No. 10,111,611, (Continued)

(51) Int. Cl.
*A61B 5/16*     (2006.01)
*G06Q 30/02*    (2012.01)
(Continued)

(52) U.S. Cl.
CPC ........... *A61B 5/165* (2013.01); *A61B 5/0077* (2013.01); *A61B 5/015* (2013.01); *A61B 5/1176* (2013.01);
(Continued)

(58) Field of Classification Search
CPC ............ G06Q 30/0271; G06Q 10/10; G06Q 30/0201; G06Q 30/0282; G06Q 50/01;
(Continued)

(56) References Cited

U.S. PATENT DOCUMENTS 3,034,500 A     5/1962   Backster, Jr.
3,548,806 A    12/1970   Fisher
(Continued)

FOREIGN PATENT DOCUMENTS

JP          08115367       7/1996
KR   10-2005-0021759 A    3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

Techniques are described for image analysis and representation for emotional metric threshold generation. A client device is used to collect image data of a user interacting with a media presentation, where the image data includes facial images of the user. One or more processors are used to analyze the image data to extract emotional content of the facial images. One or more emotional intensity metrics are determined based on the emotional content. The one or more emotional intensity metrics are stored into a digital storage component. The one or more emotional intensity metrics, obtained from the digital storage component, are coalesced into a summary emotional intensity metric. The summary emotional intensity metric is represented.

24 Claims, 27 Drawing Sheets

Related U.S. Application Data which is a continuation-in-part of application No. 13/153,745, filed on Jun. 6, 2011, now abandoned.

(60) Provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/844,478, filed on Jul. 10, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | |
|---|---|
| *G16H 50/20* | (2018.01) |
| *G16H 30/40* | (2018.01) |
| *G06Q 50/00* | (2012.01) |
| *G06F 19/00* | (2018.01) |
| *A61B 5/00* | (2006.01) |
| *A61B 5/18* | (2006.01) |
| *A61B 5/1171* | (2016.01) |
| *A61B 5/01* | (2006.01) |
| *G16H 40/67* | (2018.01) |
| *G06Q 10/10* | (2012.01) |
| *A61B 3/113* | (2006.01) |
| *A61B 5/08* | (2006.01) |
| *A61B 5/024* | (2006.01) |
| *A61B 5/0205* | (2006.01) |
| *A61B 5/11* | (2006.01) |
| *A61B 5/053* | (2006.01) |

(52) U.S. Cl.
CPC ............ *A61B 5/18* (2013.01); *A61B 5/4833* (2013.01); *A61B 5/4842* (2013.01); *A61B 5/7264* (2013.01); *A61B 5/7275* (2013.01); *G06F 19/3418* (2013.01); *G06F 19/3481* (2013.01); *G06Q 10/10* (2013.01); *G06Q 30/0201* (2013.01); *G06Q 30/0271* (2013.01); *G06Q 30/0282* (2013.01); *G06Q 50/01* (2013.01); *G16H 30/40* (2018.01); *G16H 40/67* (2018.01); *G16H 50/20* (2018.01); *A61B 3/113* (2013.01); *A61B 5/02055* (2013.01); *A61B 5/02405* (2013.01); *A61B 5/0533* (2013.01); *A61B 5/08* (2013.01); *A61B 5/11* (2013.01); *A61B 5/6824* (2013.01)

(58) Field of Classification Search
CPC ..... A61B 5/015; A61B 5/1176; A61B 5/4842; A61B 5/18; A61B 5/0077; A61B 5/7264; A61B 5/4833; A61B 5/7275; A61B 5/6824; A61B 5/0533; A61B 5/11; A61B 5/02055; A61B 5/02405; A61B 5/08; A61B 3/113; G06F 19/3481; G06F 19/3418; G16H 30/40; G16H 50/20; G16H 40/67

See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,410,609 A * | 4/1995 | Kado ................. G06K 9/00288 340/5.83 |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |

(56) References Cited

U.S. PATENT DOCUMENTS

| | | | |
|---|---|---|---|
| 7,003,135 B2 | 2/2006 | Hsieh et al. | |
| 7,013,478 B1 | 3/2006 | Hendricks et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 | 1/2008 | Mummareddy et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |
| 8,022,831 B1 | 9/2011 | Wood-Eyre | |
| 8,219,438 B1 | 7/2012 | Moon et al. | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 10,178,218 B1* | 1/2019 | Vadodaria | H04W 4/50 |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1* | 5/2003 | Dimitrova | H04N 7/163 725/10 |
| 2003/0182123 A1 | 9/2003 | Mitsuyoshi | |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0019224 A1 | 1/2006 | Behar et al. | |
| 2006/0143647 A1 | 6/2006 | Bill | |
| 2006/0170945 A1 | 8/2006 | Bill | |
| 2006/0235753 A1 | 10/2006 | Kameyama | |
| 2007/0139512 A1* | 6/2007 | Hada | H04M 11/085 348/14.01 |
| 2007/0167689 A1 | 7/2007 | Ramadas et al. | |
| 2007/0173733 A1 | 7/2007 | Le et al. | |
| 2007/0239787 A1 | 10/2007 | Cunningham et al. | |
| 2007/0255831 A1 | 11/2007 | Hayashi et al. | |
| 2007/0265507 A1 | 11/2007 | de Lemos | |
| 2007/0299964 A1 | 12/2007 | Wong et al. | |
| 2008/0059570 A1 | 3/2008 | Bill | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0287821 A1 | 11/2008 | Jung et al. | |
| 2008/0292151 A1 | 11/2008 | Kurtz et al. | |
| 2009/0002178 A1 | 1/2009 | Guday et al. | |
| 2009/0003709 A1* | 1/2009 | Kaneda | G06K 9/4628 382/190 |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0150919 A1 | 6/2009 | Lee et al. | |
| 2009/0156907 A1 | 6/2009 | Jung et al. | |
| 2009/0164132 A1 | 6/2009 | Jung et al. | |
| 2009/0193344 A1 | 7/2009 | Smyers | |
| 2009/0210290 A1 | 8/2009 | Elliott et al. | |
| 2009/0217315 A1 | 8/2009 | Malik et al. | |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0285456 A1* | 11/2009 | Moon | G06K 9/00335 382/118 |
| 2009/0299840 A1 | 12/2009 | Smith | |
| 2010/0070523 A1 | 3/2010 | Delgo et al. | |
| 2010/0099955 A1 | 4/2010 | Thomas et al. | |
| 2010/0266213 A1 | 10/2010 | Hill | |
| 2010/0274847 A1 | 10/2010 | Anderson et al. | |
| 2010/0324437 A1 | 12/2010 | Freeman | |
| 2011/0126226 A1 | 5/2011 | Makhlouf | |
| 2011/0134026 A1 | 6/2011 | Kang et al. | |
| 2011/0143728 A1* | 6/2011 | Holopainen | G06K 9/00308 455/414.1 |
| 2011/0144971 A1 | 6/2011 | Danielson | |
| 2011/0196855 A1 | 8/2011 | Wable et al. | |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2011/0296324 A1* | 12/2011 | Goossens | G06Q 10/10 715/763 |
| 2012/0324491 A1 | 12/2012 | Bathiche et al. | |
| 2013/0023337 A1 | 1/2013 | Bowers et al. | |
| 2013/0116587 A1 | 5/2013 | Sommo et al. | |
| 2013/0197409 A1 | 8/2013 | Baxter et al. | |
| 2014/0142397 A1* | 5/2014 | Bedrosian | A61B 5/024 600/301 |
| 2014/0172910 A1 | 6/2014 | Jung et al. | |
| 2014/0356832 A1* | 12/2014 | Duffy | A61B 5/16 434/236 |
| 2015/0279224 A1* | 10/2015 | Dahlkvist | G06F 16/31 434/236 |
| 2016/0104486 A1 | 4/2016 | Penilla et al. | |
| 2017/0003784 A1 | 1/2017 | Garg et al. | |
| 2020/0074156 A1* | 3/2020 | Janumpally | G06K 9/00255 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

(56) References Cited

OTHER PUBLICATIONS

International Search Report dated May 24, 2012 for PCT/US2011/060900.
Xiaoyu Wang, An HOG-LBP human detector with partial occlusion handling, Sep. 29, 2009, IEEE 12th International Conference on Computer Vision, Kyoto, Japan.
Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.
Nicholas R. Howe and Amanda Ricketson, Improving the Boosted Correlogram, 2004, Lecture Notes in Computer Science, ISSN 0302-9743, Springer-Verlag, Germany.
Xuming He, et al, Learning and Incorporating Top-Down Cues in Image Segmentation, 2006, Lecture Notes in Computer Science, ISBN 978-3-540-33832-1, Springer-Verlag, Germany.
Ross Eaton, et al, Rapid Training of Image Classifiers through Adaptive, Multi-frame Sampling Methods, Oct. 2008, IEEE 37th Applied Imagery Pattern Recognition Workshop, Washington DC.
Verkruysse, Wim, Lars O. Svaasand, and J. Stuart Nelson. "Remote plethysmographic imaging using ambient light." Optics express 16.26 (2008): 21434-21445.
Albiol, Alberto, et al. "Face recognition using HOG-EBGM." Pattern Recognition Letters 29.10 (2008): 1537-1543.
Fasel, B. (Aug. 2002). Robust face analysis using convolutional neural networks. In Object recognition supported by user interaction for service robots (vol. 2, pp. 40-43). IEEE.
Matsugu, M., Mori, K., Mitari, Y., & Kaneda, Y. (2003). Subject independent facial expression recognition with robust face detection using a convolutional neural network. Neural Networks, 16(5-6), 555-559.

\* cited by examiner

IMAGE ANALYSIS FOR EMOTIONAL METRIC EVALUATION

RELATED APPLICATIONS

This application claims the benefit of U.S. provisional patent applications "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

This application is also a continuation-in-part of U.S. patent application "Personal Emotional Profile Generation" Ser. No. 14/328,554, filed Jul. 11, 2014, which claims the benefit of U.S. provisional patent applications "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014.

The application "Personal Emotional Profile Generation" Ser. No. 14/328,554, filed Jul. 11, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The foregoing applications are each hereby incorporated by reference in their entirety.

FIELD OF INVENTION

This application relates generally to image analysis and more particularly to image analysis and representation for emotional metric threshold evaluation.

BACKGROUND

People spend seemingly endless amounts of time engaging with the Internet. While some of that time is spent in productive, informational, or educational pursuits, other amounts of time—sometimes vast amounts—are consumed viewing, interacting with, or "surfing" for web content that may be found on the nearly two billion websites currently available. The websites, and the webpages hosted on the websites, contain a wide variety of content with which the people choose to engage. The content includes news, shopping, sports, entertainment, politics, cute puppy videos, and much, much more. People use a variety of electronic devices to engage with the many, many types of online content. Website analytics, commonly referred to simply as "web analytics", have been performed to collect, measure, analyze, and report useful information related to a given website. The website information is analyzed to understand how people use the website and to optimize the manner in which the website can be used. Web analytics are often used by both the enterprises that manage the websites and various market research groups to measure operational performance. So, whether the enterprise is launching a new product, or the marketing research group is testing their advertising campaign, web analytics are used to determine website engagement and effectiveness.

While web analytics describe part of a person's interaction with webpages, websites, and other content, the analytics tell only part of the story. People can experience cognitive states, mental states, moods, or emotions as they surf the web. Much work has been done in recent years using computer-based techniques to detect human emotions or moods. These techniques routinely rely on advanced image processing. The image processing is performed on images of the human face. The facial expressions generated by a human experiencing an emotion often occur subconsciously. When detected, the facial expressions can convey the emotions, feelings, and sentiments that a person is currently experiencing.

The evaluation of the cognitive states of individuals who are visiting a webpage is key to understanding the individuals and the ways that they react to the world around them. Cognitive states run the gamut from happiness to sadness, from contentedness to worry, from excitement to calmness, from boredom to attentiveness, among numerous others. These cognitive states are experienced in response to everyday events such as frustration which stuck a traffic jam, boredom while waiting in line, impatience while waiting for that first cup of coffee, and even various cognitive states as people interact with their computers and the internet. Individuals perceive and empathize with other people by consciously or unconsciously evaluating and understanding the cognitive states of those other people. For example, an empathetic person may perceive in another person anxiety or joy and may respond accordingly. The ability and means by which one person perceives the emotional state of another is often quite difficult to summarize and has often been communicated as visceral or as a "gut feel." Yet, automated evaluation of the cognitive states of people is far more challenging.

Cognitive states, such as confusion, concentration, and worry, may be identified to aid in the understanding of an individual or group of people. People can collectively respond with fear or anxiety, such as after witnessing a catastrophe. Similarly, people can collectively respond with happy enthusiasm, such as when their sports team obtains a victory. Certain facial expressions and head gestures may be used as cues to identify a cognitive state that a person is experiencing. Limited automation has been performed in the evaluation of cognitive states based on facial expressions. Certain physiological conditions may provide telling indications of a person's state of mind and have historically been evaluated in a crude fashion, as with an apparatus used for lie detection or polygraph tests.

SUMMARY

Image analysis is used for emotional metric threshold evaluation. Image data is collected at a client device of a user interacting with a media presentation. The media presentation can include live-feed or live-streamed video, a video channel, still images, audio, and so on. The image data that is collected includes facial images of the user. One or more processors are used for analyzing the image data to extract emotional content of the facial images. The one or more processors can be coupled to the client device, or can be local processors, remote processors, cloud processors, mesh processors, etc. The emotional content can include one or more of one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. One or more emotional intensity metrics are determined based on the emotional content. The emotional intensity metric can be based on the Facial Action Coding System (FACS) and can range from A (trace) to E (maximum). The one or more emotional intensity metrics are stored in a digital storage component. The storage component can be coupled to the client device, or can consist of a local, remote, cloud, or other storage component, etc. The one or more emotional intensity metrics, obtained from the storage component, are coalesced into a summary emotional intensity metric. The coalescing of the emotional intensity metrics can include counting occurrences of a specific emotion type within the emotional content. The summary emotional intensity metric is represented. The representing can include displaying the summary emotional intensity metric or the one or more emotional intensity metrics. The screen can be coupled to the client device, can be visible by the client using the client device, and so on.

In embodiments, a computer program product embodied in a non-transitory computer readable medium for image analysis comprises code which causes one or more processors to perform operations of: collecting, at a client device, image data of a user interacting with a media presentation, wherein the image data comprises facial images of the user; analyzing, using one or more processors, the image data to extract emotional content of the facial images; determining one or more emotional intensity metrics based on the emotional content; storing the one or more emotional intensity metrics into a digital storage component; coalescing the one or more emotional intensity metrics, obtained from the storage component, into a summary emotional intensity metric; and representing the summary emotional intensity metric.

In other embodiments, a computer program product embodied in a non-transitory computer readable medium for image analysis comprises code which causes one or more processors to perform operations of: collecting, at a client device, image data of a user interacting with a media presentation, wherein the image data comprises facial images of the user; analyzing, using one or more processors, the image data to extract emotional content of the facial images; determining one or more emotional intensity metrics based on the emotional content; storing the one or more emotional intensity metrics into a digital storage component; detecting that a threshold value has been met by the one or more emotional intensity metrics; generating a graphical representation of a facial expression for the user based on the threshold value having been met; and attaching the graphical representation to a representation of the media presentation.

In some embodiments, a computer system for image analysis comprises: a memory which stores instructions; one or more processors attached to the memory wherein the one or more processors, when executing the instructions which are stored, are configured to: collect, at a client device, image data of a user interacting with a media presentation, wherein the image data comprises facial images of the user; analyze, using one or more processors, the image data to extract emotional content of the facial images; determine one or more emotional intensity metrics based on the emotional content; store the one or more emotional intensity metrics into a digital storage component; coalesce the one or more emotional intensity metrics, obtained from the storage component, into a summary emotional intensity metric; and represent the summary emotional intensity metric.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
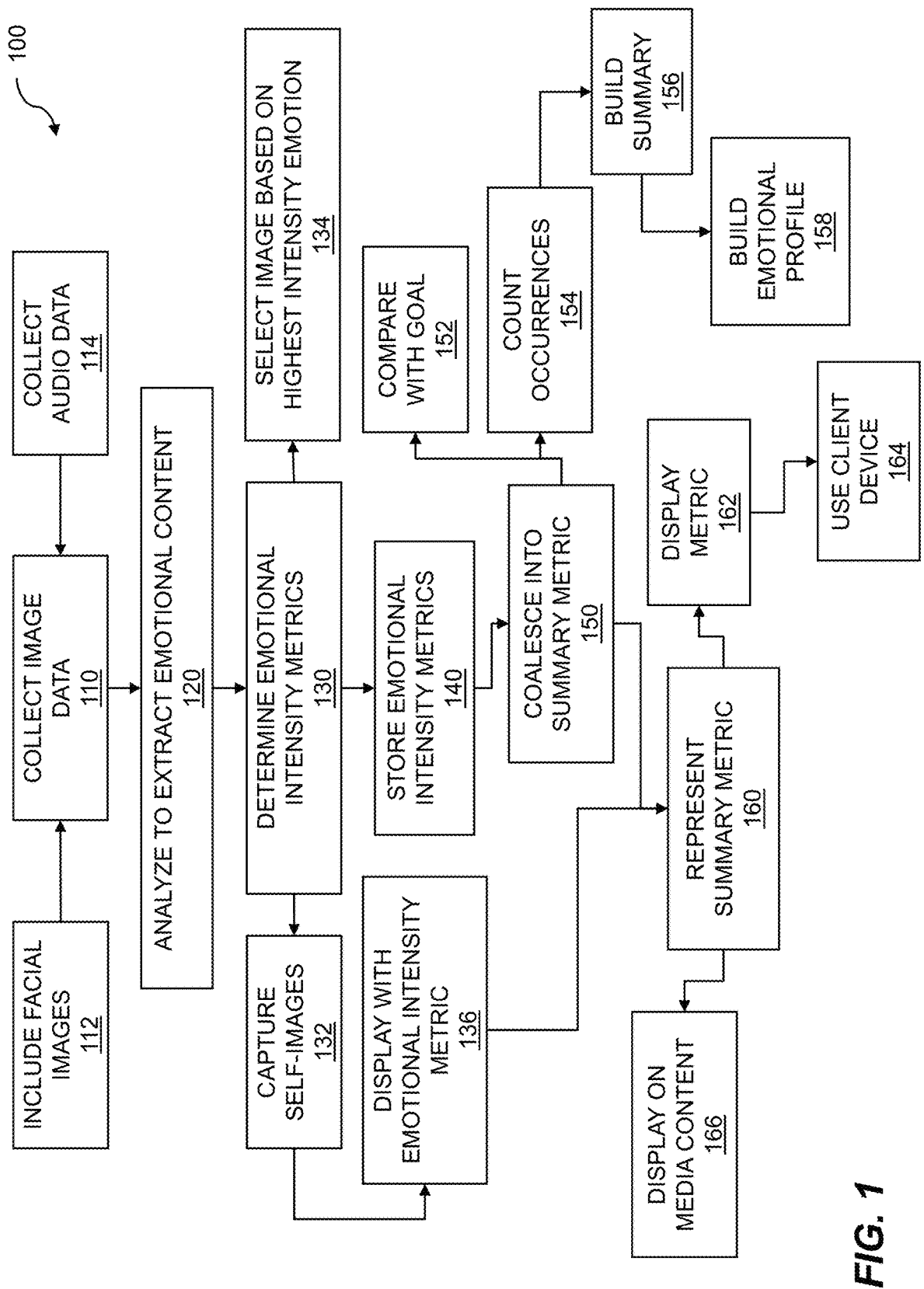
FIG. 1 is a flow diagram for image analysis and representation for emotional metric threshold evaluation.

Humans immersed in a given environment, whether urban, rural, virtual, or augmented, are continuously experiencing their surroundings through the use of their senses. They observe and process external stimuli using sight, hearing, smell, touch, and so on. A significant part of human interaction is based on observing one another's faces. To this end, sight plays an integral role in social interaction. Because the human face is so highly expressive, one's ability to observe the face of another person during social interaction is critical. The myriad facial expressions that can be exhibited range widely and can convey or indeed unveil a person's true emotional, cognitive, or mental state. For example, while a sultry smile communicates one message to the recipient of the smile, an angry frown communicates quite a different one. In another example, a neutral expression can indicate ennui, inattention, indifference, lassitude, and so on. The effective communication of information that is the basis of this social exchange among the participants in the interaction greatly influences how the interaction progresses. A smile may attract people to the interaction and may hold their attention, while the angry frown can cause people to leave the interaction, perhaps expediently.

Humans commonly interact with each other through the use of electronic devices. Individuals use a range of devices daily, such as smartphones, personal digital assistants, tablets, laptops, and so on. The individuals use these devices to share content and to view and interact with websites, streaming media, social media, and many other channels. The channels can include social media sharing which can induce emotions, moods, cognitive states, and mental states in the individuals. The channels can inform, amuse, entertain, annoy, anger, bore, distress, etc., those who view the channels. As a result, the emotion of a given individual can be directly impacted by the media channels viewed by the individual, and by the reactions shared and displayed by the individual's friends, followers, and those whom the individual follows, etc. The individual may enjoy pursuing content that makes her or him happy, but may wish to skip content they find to be boring, and may want to avoid altogether content that angers, annoys, disgusts, or disquiets them.

Various emotional metrics of an individual can be determined by using a device such as a client device to capture image data including facial data. The image data can include self-images ("selfies"), candid images, or unposed shots of the individual as she or he interacts with a media presentation. The media presentation can be a video, video clip, video frame, still image, graphics interchange format (GIF) animation, etc. The media presentation can be presented through a webpage, a web portal, a social media site, and the like. The self-images can be captured at random times in order to collect the genuine emotion of the individual at the time the self-image is captured. By analyzing the facial data, emotional intensity metrics can be determined. A summary emotional intensity metric can be determined by coalescing the emotional intensity metrics. These emotional intensity metrics, along with the summary emotional intensity metric, can be displayed to the individual. The individual can use the summary emotional intensity metric or the emotional intensity metrics to share emotions, moods, cognitive states, or mental states, self-images, etc., with friends and followers through social media sharing. The emotional intensity metrics can be used to make recommendations to the user to meet emotional intensity goals, to improve a mood, to show the individual's prevailing emotion on a certain day, to display progress toward daily emotion goals, and so on.

In disclosed techniques, image analysis and representation is used for emotional metric threshold evaluation. Image data, including facial data, is collected at a client device of a user as the user interacts with a media presentation. Processors are used to analyze the image data in order to extract emotional content of the facial images. Emotional intensity metrics are determined based on the emotional content, and the emotional intensity metrics are stored in digital storage. The emotional intensity metrics are coalesced into a summary emotional intensity metric. The summary emotional intensity metric is represented. In embodiments, the representing includes displaying the summary emotional intensity metric or the one or more emotional intensity metrics.

FIG. 1 is a flow diagram for image analysis and representation for emotional metric threshold evaluation. The flow 100 includes collecting, at a client device, image data 110 of a user interacting with a media presentation, where the image data includes facial images 112 of the user. The image data including the facial images 112 can be collected using a camera coupled to the client device or other camera to which there is a line of sight from the user. The capturing of image state data and facial images can include using a video camera, a still camera, a thermal imager, a CCD device, a phone camera, a three-dimensional camera, a depth camera, a light field (plenoptic) camera, multiple cameras used to show different views of an individual, or any other type of image capture apparatus that can allow captured data to be used in an electronic system. In embodiments, the image data includes buffered image frames. The image frames can be buffered on the client device, on a local processor, on a remote processor such as a server, etc. The contents of the buffer can be based on an amount of time. In embodiments, the image frames can transpire over two seconds of time.

The collecting can include unposed or candid facial images of the user. The unposed facial images can be collected at random times, at certain times, at times when the user is looking at the media presentation, at times when the user reacts to the media presentation, and so on. In embodiments, media presentation can include a webpage, a social networking page, or a shared social video channel. The media content be provided via a website, a streaming site, an app, etc. The collecting can include augmenting the collected image data by collecting audio data 114. The audio data can include ambient sounds, human-generated sounds, and so on. In embodiments, the audio data can include speech. The audio data and the speech data can be collected using a microphone, a transducer, or other audio capture apparatus. The audio data can include noises and sounds made by the user. In embodiments, the audio data can include non-speech vocalizations. The non-speech vocalizations can include grunts, yelps, squeals, snoring, sighs, laughter, giggles, filled pauses, unfilled pauses, groans, sudden outbursts, whistles, or yawns.

The flow 100 includes analyzing, using one or more processors, the image data to extract emotional content 120 of the facial images. The one or more processors can be coupled to the client device or can be coupled to a local server, remote server, cloud server, distributed server, mesh server, server as a service, and so on. The emotional content can include an emotion type, where the emotion type can include of one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The flow 100 includes determining one or more emotional intensity metrics 130 based on the emotional content. The emotional intensity metrics can be based on the facial action coding system (FACS). The intensity scoring of FACS can describe the movements of facial muscles as A trace, B slight, C marked or pronounced, D severe or extreme, and E maximum. The movements of the facial muscles can be used to categorize outward and physical expressions of various emotions.

The determining the emotional intensity metrics can be used for a variety of purposes. In embodiments, the flow 100 includes capturing self-images 132 of the user based on the emotional intensity metric. The self-images, now commonly referred to as "selfies", can be captured using a camera or other image capture device coupled to the client device, a camera with a line of sight to the user, etc. The self-images can be captured as the user interacts with the media presentation. The self-images can include video clips of the user. The self-images can be captured at various points in time, including random points in time, in order to capture candid images of the user. The candid self-images can capture the genuine emotions of the user rather than the posed images which may not. The flow 100 includes selecting an image from the facial images 134, where the image that was selected is based on a highest intensity emotion. The highest intensity emotion could be a smile, a frown, a smirk, a grimace, and so on. As discussed shortly, the image that was selected, based on the highest intensity emotion, can be displayed. In embodiments, the flow 100 includes displaying the self-images along with the summary emotional intensity metric 136. Displaying of the image is discussed shortly. The flow 100 includes storing the one or more emotional intensity metrics 140 in a digital storage component. The digital storage component can be coupled to the client device, a local server, a remote server, a cloud server, or other server, as discussed throughout. The storage component can include a flash memory, a solid-state disk (SSD), or other media suitable for storing the emotional intensity metrics and other data.

The flow 100 includes coalescing 150 the one or more emotional intensity metrics, obtained from the storage component, into a summary emotional intensity metric. The coalescing the one or more emotional intensity metrics can include a variety of techniques including arithmetical, statistical, algorithmic, or heuristic techniques. The coalescing can be based on voting by the user of the client device, the user of an app, other users who use the app, and so on. In embodiments, the collecting, analyzing, determining, and coalescing comprise a content delivery system. The content delivery system can include a social media network, portal, website, or app. The summary emotional intensity metric can be used for a variety of purposes. In embodiments, using the summary emotional intensity metric includes comparing the summary emotional intensity metric to an emotional intensity goal 152. The emotional intensity goal can include a daily goal, a weekly goal, a monthly goal, etc. The emotional intensity goal can include reducing a daily percentage of an emotion such as anger, increasing the daily percentage of an emotion such as happiness, and so on. In the flow 100, the coalescing further includes counting occurrences 154 of a specific emotion type within the emotional content. The counting can be over a period of time such as counting events per hour, per day, and so on. The counting events can include multiple emotion types, such as anger, boredom, happiness, goofiness, etc. The flow 100 includes building the summary 156 emotional intensity metric based on a number of the occurrences. The number of occurrences can include the number of occurrences for a single emotional intensity metric or a plurality of emotional intensity metrics. The number of occurrences can include an average of the number of occurrences of a plurality of emotional intensity metrics. The flow 100 includes building an emotional profile 158 based on the summary emotion intensity metric. The emotional profile can be for the user of the client device. The emotional profile can include information such as preferences for media presentations, likes and dislikes, app preferences, app settings, and so on. The emotional profile can include other data such as age, gender, ethnicity, geographic location, etc.

The flow 100 includes representing 160 the summary emotional intensity metric. The representing of the summary emotional intensity metric can include an image such as an image of the user, an emoji, an emoticon, an animated emoji, a cartoon, and so on. In embodiments, the representing can include displaying the summary emotional intensity metric 162 or the one or more emotional intensity metrics. The displaying can include rendering the representation on a display. The display can include an electronic display coupled to a device such as a smartphone, a personal digital assistant (PDA), a tablet computer, a laptop computer, television, projector, etc., which is within a line of sight of the user. The displaying can include displaying the self-images along with the summary emotional intensity metric. The self-images can include one or more video frames, video clips, videos, gifs, and so on. In embodiments, the summary emotional intensity metric can be displayed on the client device 164. The emotional intensity metric can be displayed using a webpage, an app, and so on. In other embodiments, the flow 100 further includes displaying information on the content of the media presentation 166. Similar to the displaying of the summary emotional intensity metric, the media presentation can be displayed using a webpage, and app, and so on. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
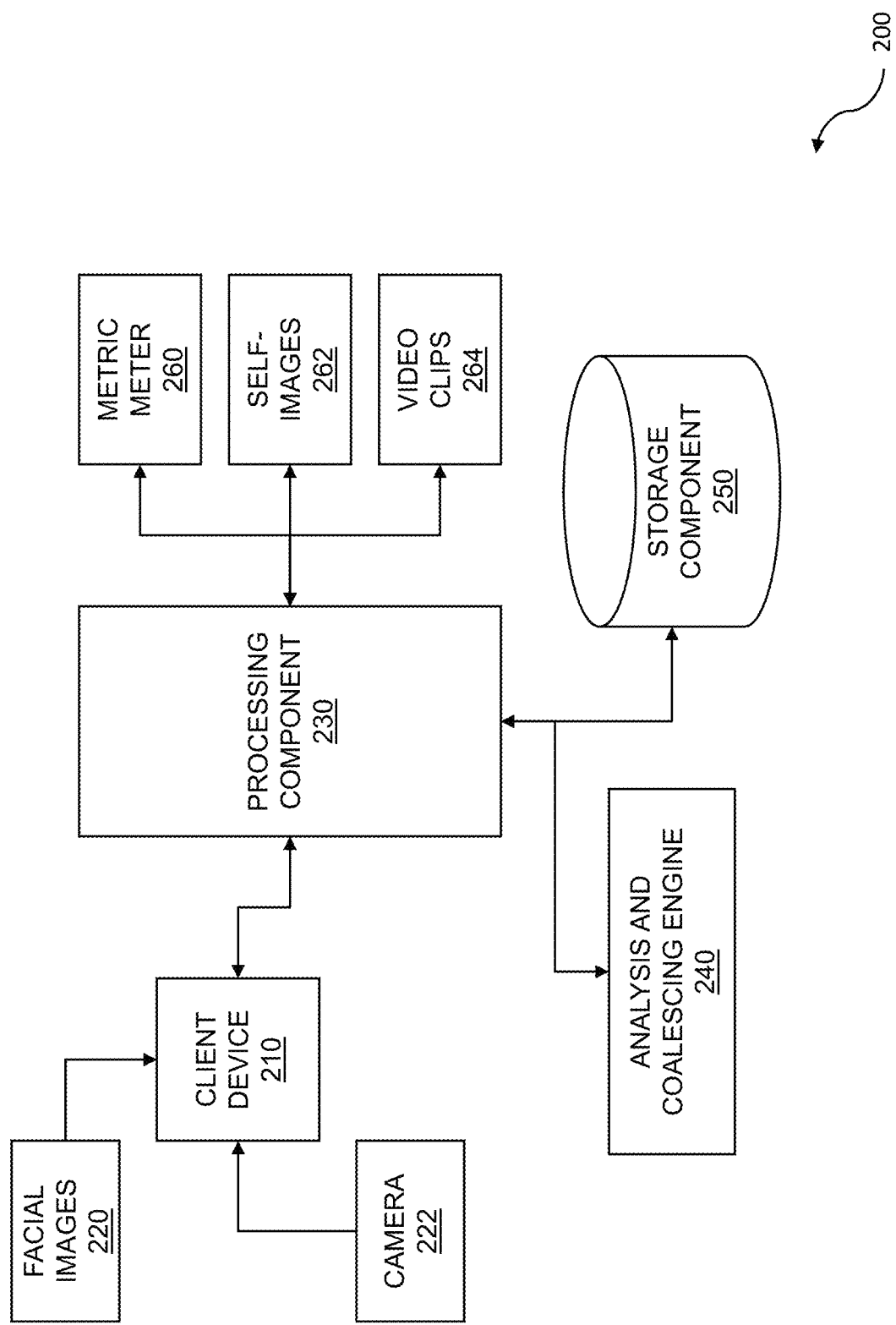
FIG. 2 illustrates a system for facial analysis and metric/output generation.

FIG. 2 illustrates a system 200 for facial analysis and metric/output generation. Image analysis and representation are performed for emotional metric target evaluation. Image data is collected at a user device 210. The image data, including facial images 220, can be of a user interacting with a media presentation. The media presentation can include an advertisement, a political message, educational materials, a news feed, and so on. The media presentation can include social content such as social media, livestreamed video or audio, and the like. The facial images can be captured with a camera 222 that is coupled to the client device. A camera can include a webcam, a video camera, a still camera, a thermal imager, a CCD device, a phone camera, a three-dimensional camera, a depth camera, a plenoptic camera, multiple webcams used to show different views of a person, or any other type of image capture apparatus that can allow captured data to be used in an electronic system. In some embodiments, the user can obtain an app and can "opt-in" to the image data and facial image collection. For example, the person can agree to the capture of facial images using a personal device such as a mobile device or another electronic device by selecting the opt-in choice. Opting-in can then activate the person's webcam-enabled device and can begin the capture of the person's facial images and data via a video feed from the webcam or other camera. One or more processors can include a processing component 230 and can be used to analyze the image data to extract emotional content of the facial images. The emotional content can include an emotion type, where the emotion type can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The analyzing and coalescing can be performed on the processing component by implementing an analysis and coalescing engine 240. Emotional intensity metrics can be determined based on the emotional content. The emotional intensity metrics can include counting occurrences of a specific emotion type within the emotional content. The emotional intensity metrics can include a time for onset of an emotion type, a duration time, a decay time, an intensity value, etc. The emotional intensity metrics can be based on the facial action coding system, where the intensity can range from A (trace) to E (maximum). Digital storage components 250 can be used to retain the one or more emotional intensity metrics, a coalesced or summary emotional intensity metric, or the like. The storage components can include memory coupled to the client device, a local server, a remote server, cloud storage, distributed storage, mesh storage, etc. The emotional intensity metrics, obtained from the one or more storage components, can be coalesced into a summary emotional intensity metric. The coalescing of the emotional intensity metrics can be performed using the analysis and coalescing engine 240. The summary emotional intensity metric can include video clips of the user as she or he reacts to one or more media presentations over a period of time. The summary emotional intensity metric can be represented. The representing can include displaying the summary emotional intensity metric or the one or more emotional intensity metrics. The displaying can be rendered on a screen, where the screen can be associated with the client device, a screen in view of the user, and so on. The display on the screen can include a metric meter 260. The metric meter can include a mood meter, and can display moods such as happy, sad, angry, confused, etc. The metric meter can include goals, events, achievements, and so on. The display on the screen can include self-images 262. The self-images, commonly referred to as "selfies", can include still images, videos, video clips, and so on. The display on the screen can include video clips 264. The video clips can include composite videos which incorporate various self-images, emotions, moods, reactions, etc., of the user over a period of time. The video clips can include emojis, animated emojis, emoticons, animated emoticons, graphics interchange format (GIF) files, cartoons, and so on.

Figure 3:
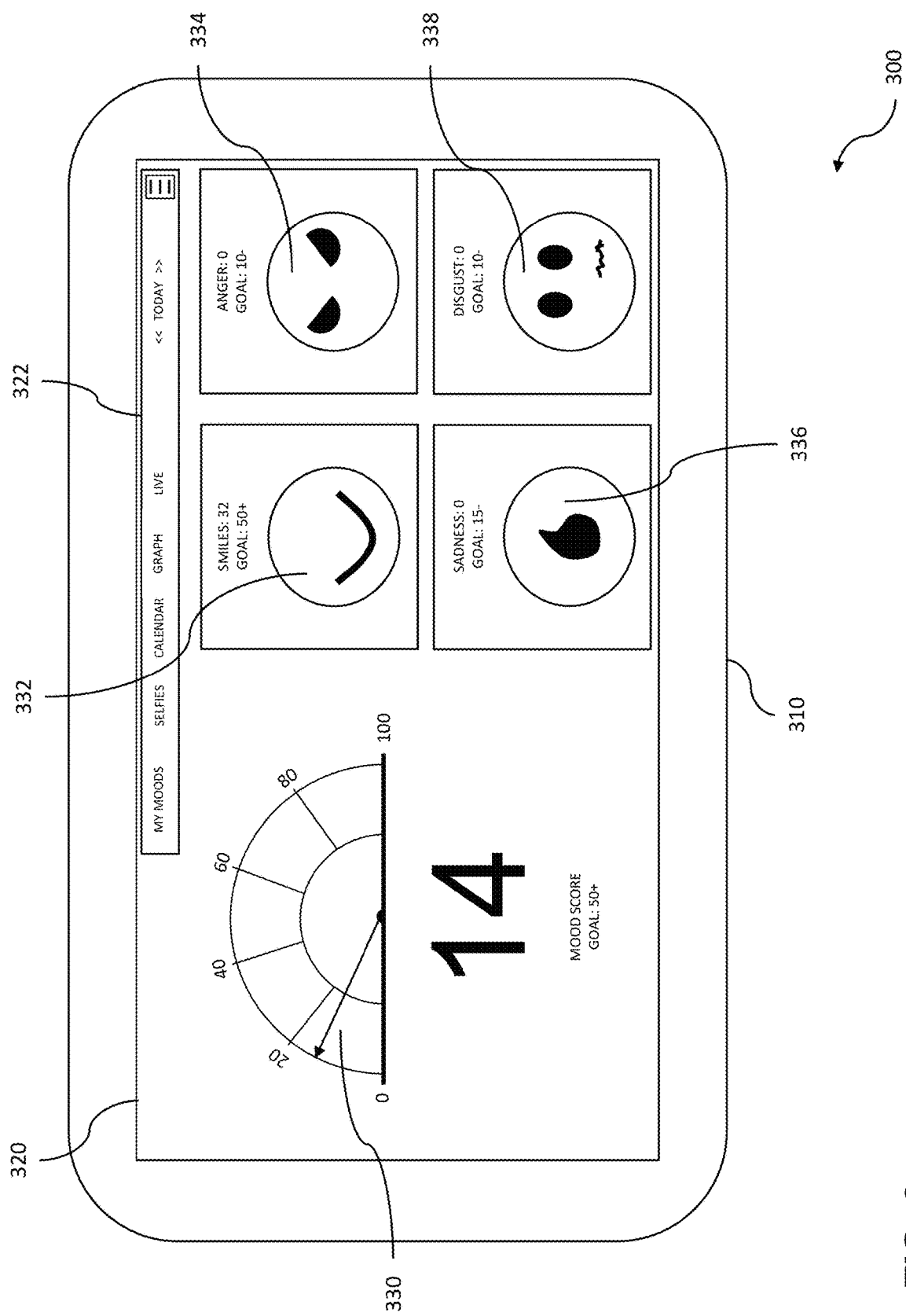
FIG. 3 shows an example mood meter with moods and scores.

FIG. 3 shows an example mood meter with moods and scores. A mood meter can be used to display information to an individual, where the information that is displayed is based on image analysis and representation for emotional metric threshold evaluation. Image data that includes facial images is collected at a client device. The image data and the facial images are collected of a user interacting with a media presentation. Processors are used to analyze the image data to extract emotional content of the facial images. Emotional intensity metrics are determined based on the emotional content, and the emotional intensity metrics are stored in a digital storage component. The emotional intensity metrics are coalesced into a summary intensity metric, and the summary intensity metric is represented. A mood meter with moods and scores is shown 300. The mood meter, moods, and scores can be displayed on a client device 310, where the client device can include a smartphone, personal digital assistant (PDA), tablet, laptop computer, and so on. The client device can include a camera such as a webcam. The display 320 can include a menu 322 for displaying moods, checking self-images ("selfies"), a calendar, a graph, a live stream that includes video or audio, a calendar, display and other settings, etc. The displayed content shown on the display 320 can include the mood meter 330 which can show moods, an attained mood score, a goal, and so on. The displayed content can include one or more moods. The one or more moods can include a goal or target, a count of mood occurrences, indicators such as colors, emojis, emoticons, and the like, to monitor progress toward the goal or target, and the like. The moods can include a range of moods such as smiles 332, anger 334, sadness 336, disgust 338, etc. The goals displayed for the moods can include a daily goal, a target, a score, and so on.

Figure 4:
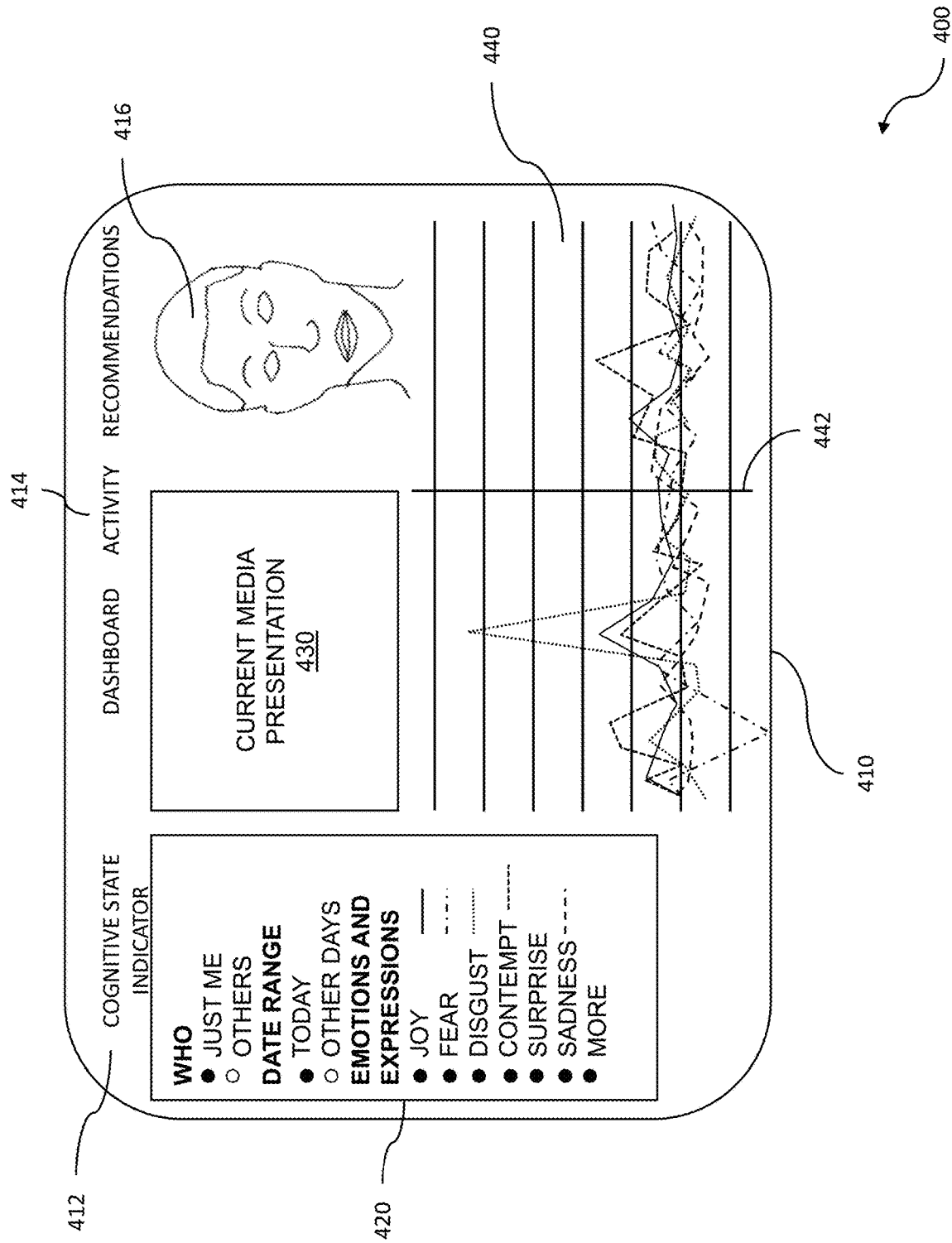
FIG. 4 illustrates an example dashboard for individual activity.

FIG. 4 illustrates an example dashboard for individual activity. A dashboard for individual activity can be based on image analysis and representation for emotional metric threshold evaluation. A client device can be used to collect image data including facial images of a user interacting with a media presentation. Processors can be used to analyze the image data to extract emotional content of the facial images. Emotional intensity metrics can be determined based on the emotional content. Digital storage components can retain the one or more emotional intensity metrics. The emotional intensity metrics, obtained from the digital storage component, can be coalesced into a summary emotional intensity metric. The summary emotional intensity metric can be represented. The representing can include showing the summary emotional intensity metric on a display.

An example dashboard 400 shows individual activity 410. The dashboard can include a variety of fields, panes, settings, etc., where the fields can be configured by a content provider, configured by the individual, and so on. The dashboard can include a title 412 for the dashboard. The dashboard can comprise fields 414, where the fields can include pulldown menus, radio buttons, settings, adjustments, etc., which can be used to display cognitive state and other information to the individual. The dashboard can include controls for selecting among various dashboards. The dashboards can include a cognitive state dashboard, a mood dashboard, an emotional state dashboard, a mental state dashboard, etc. The dashboard can comprise a user pane 416. The user pane can show an image of the user, a video, a selfie, an emoji, a caricature, a cartoon, an animation, a selected image, and so on. A selected dashboard or default dashboard can display activity 420 of the individual. The activity of the individual can include a list of who may see a cognitive state indication, a range of dates over which cognitive state data can be shown, types of emotions, facial expressions, and so on. The activity pane can include the activity of others, a list of emotions and expressions, selfie settings, screenshot settings, and so on.

The dashboard can show a current media presentation 430. The current media presentation can include a webpage, a video, a media presentation, a social media presentation, etc. The current media can include an image of a webpage being observed by the individual. The dashboard can include moment-by-moment metrics 440, where the moment-by-moment metrics can be based on cognitive state data. The cognitive state data can be indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The moment-by-moment metrics can include physiological data that can be captured along with the collecting cognitive state data. A plurality of metrics can be displayed. A selector 442 can be used to determine values for one or metrics at a given time.

Figure 5:
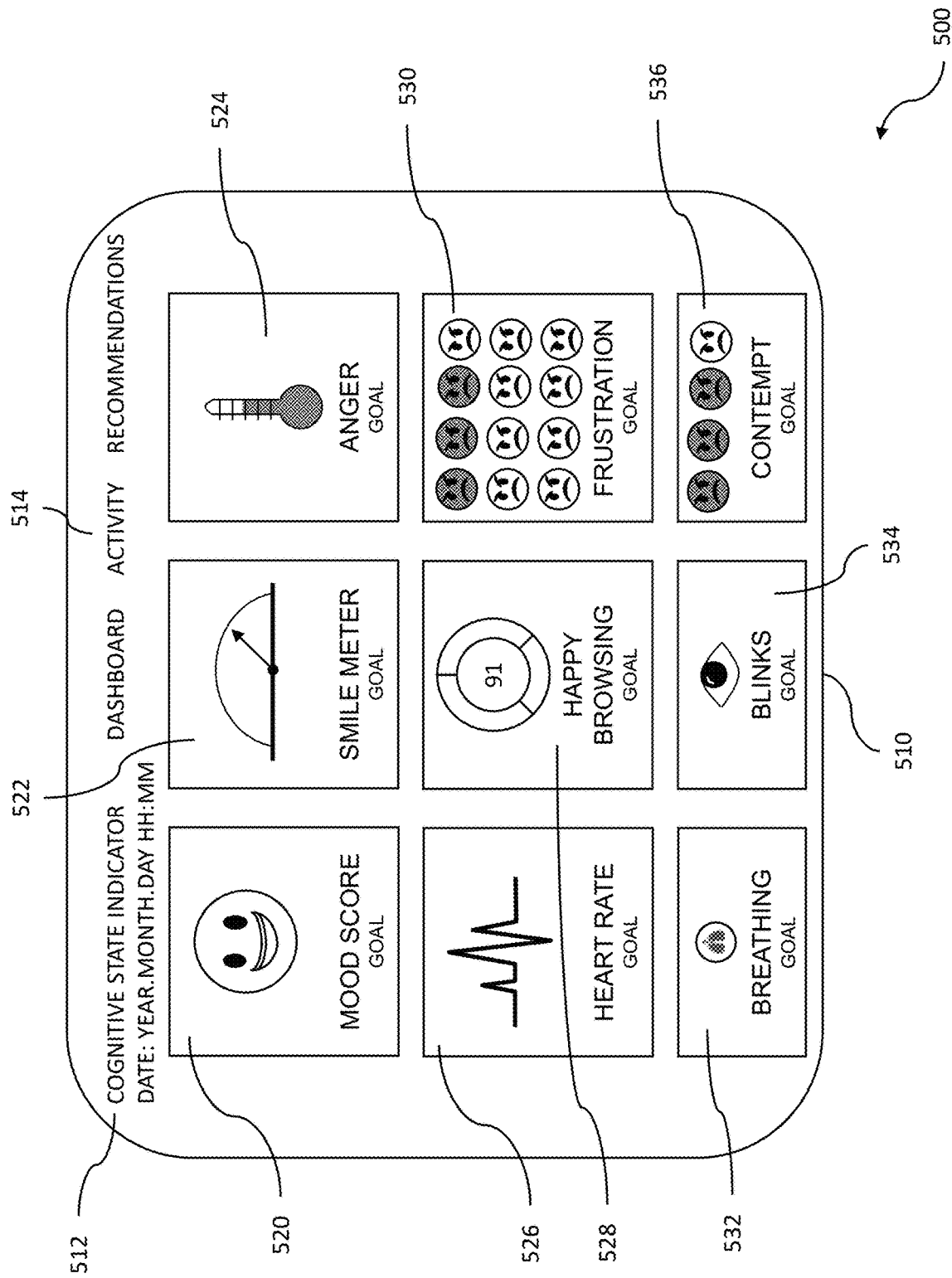
FIG. 5 shows an example dashboard of options.

FIG. 5 shows an example dashboard of options. A dashboard can be used to display a variety of information to an individual, where the information is based on image analysis and representation for emotional metric threshold evaluation. Image data, including facial images, is collected, at a client device, from a user interacting with a media presentation. Processors are used to analyze the image data to extract emotional content. Emotional intensity metrics are determined and stored in a digital storage component. The emotional intensity metrics are coalesced into a summary intensity metric, and the summary intensity metric is represented. The representing the summary emotional intensity metric can include displaying on a screen.

A dashboard 500, such as example dashboard 510, can display a variety of information to an individual. The dashboard can be rendered on a display such as a display coupled to an electronic device associated with the individual, an electronic display coupled to a vehicle, an electronic display within a line of sight to the individual, and so on. The electronic device can include a smartphone, a personal digital assistant, a tablet computer, a laptop computer, and the like. The electronic display can be coupled to a wearable electronic device such as a smart watch, smart glasses, a "heads up" display, etc. The example dashboard can include displayed information such as a mood score 520, a meter, such as a smile meter 522, and a target number of smiles per day, an anger meter 524 with daily goal, a heart rate with daily goal 526, a browsing mood such as happy browsing 528, a frustration meter and goal 530, a breathing meter and goal 532, an eye blinks meter and goal 534, a contempt meter and goal 536, and so on. The dashboard 510 can include controls 512 which can be used to select among multiple dashboards, to display time or date information, to display various activities 514, to take action or receive suggestions for such activities that would alter a mood, and so on.

Figure 6:
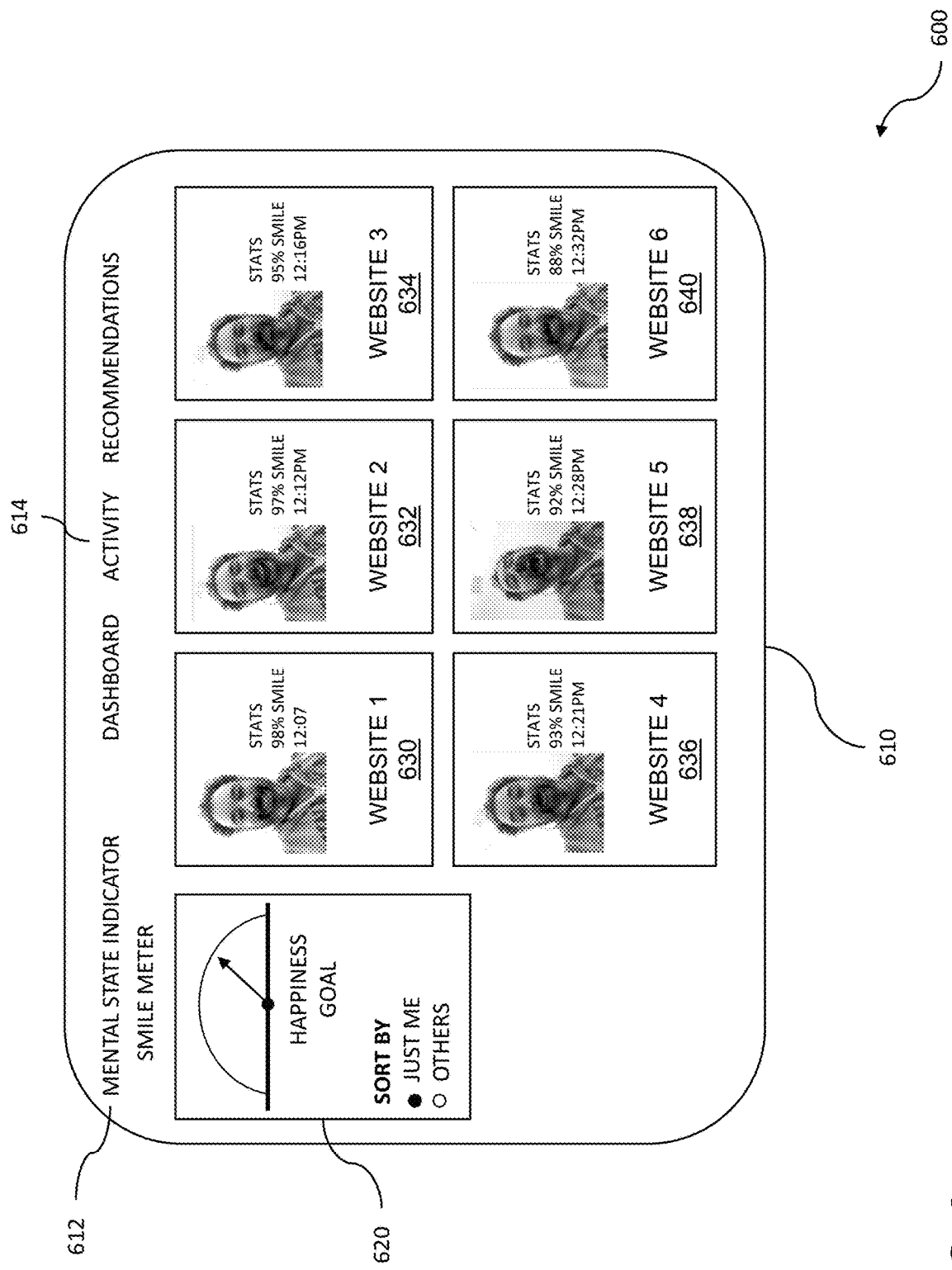
FIG. 6 illustrates a dashboard of statistical results.

FIG. 6 illustrates a dashboard of statistical results. Various statistical results can be determined using image analysis and representation for emotional metric threshold evaluation. Image data and facial images are collected from a user interacting with a media presentation. Processors are used to analyze the image data to extract emotional content. Emotional intensity metrics are determined from the emotional content, and the emotional intensity metrics are stored in digital storage components. The emotional intensity metrics are coalesced into a summary emotional intensity metric, and the summary emotional intensity metric is represented. Statistical results 600 based on the analyzing and the determining can be displayed to an individual using a dashboard 610. The dashboard can include a mood dashboard. The dashboard can display statistical results for a variety of cognitive states, mental states, emotions, moods, etc., such as happy, sad, confused, angry, annoyed, concentrating, bored, and so on. The dashboard can display statistical results based on a range of emotional content, emotional states, cognitive states, mental states, moods, etc. The displayed cognitive states, moods, emotions, mental states, and so on, can be based on emotional states associated with the individual or on aggregating the emotional states from the individual with cognitive state data from other individuals. The cognitive state data for the individual can be compared to the aggregated cognitive state data from the other individuals. The cognitive state data from other individuals can be based on demographics such as age, gender, race, geographic location, educational level, household income, etc.

The dashboard 610 can include controls 612. The controls 612 can be used to select various views, activities 614, actions, recommendations, and so on. The dashboard can display a variety of cognitive states, facial expressions, emotional states, mental states, moods, and the like. The facial expressions, for example, can include smiles, frowns, smirks, neutral expressions, etc. The dashboard 610, when displaying smiles, can include a smile meter 620. The smile meter can include a display for level of happiness, a goal, sorting options such as most recent smile and biggest smiles, selfie settings, screenshot settings, etc. The statistical results of a mood such as a smile can be displayed with various statistics. The statistics for smiles can include a percentage of time smiling, the time at which the smile occurred, the most intense smile, the longest smile, the website for which the smile occurred, an image of the individual for whom the statistical results are being displayed, etc.

Several renderings of statistics for emotional content, a cognitive state, emotional state, facial expression, mood, and so on, can be display simultaneously. The renderings can be associated with one or more websites. In the figure, the statistics for six websites are shown. While six renderings of statistics associated with the six websites are shown, other numbers of renderings of statistics can be displayed. The statics for website 1 630 are rendered. The rendering of the statistics for website 1 includes an image such as a selfie of the individual, statistics for a percentage smile, and the time at which the individual viewed website 1. The statistics for website 2 632 can be rendered. The individual has "surfed" from website 1 to website 2. An image of the individual is shown and a percentage smile is determined for a second time, the time at which website 2 was viewed. The individual continues surfing the web to website 3 634. The rendering for website 3 includes an image of the individual, the percentage smile, and the time at which the smile percentage was determined. The individual continues surfing the web to other websites, such as website 4 636, website 5 638, and website 6 640. For each of the websites, an image such as a selfie of the individual can be shown along with various statistics. Since the statistics include smiles, the percentages of smile analyzed and evaluated at each website are rendered along with a time stamp at which the individual viewed the website content. The percentages of smiles may change while the individual consumes web content from various websites. The percentages can change due to content that may not appeal to the individual, or the individual experiencing fatigue, distraction, and so on. Additional renderings can be displayed, where the additional renderings can be associated with cognitive states, facial expressions, emotional states, moods, etc. The other cognitive states can be indicative of drowsiness, fatigue, distraction, impairment, etc.

Figure 7:
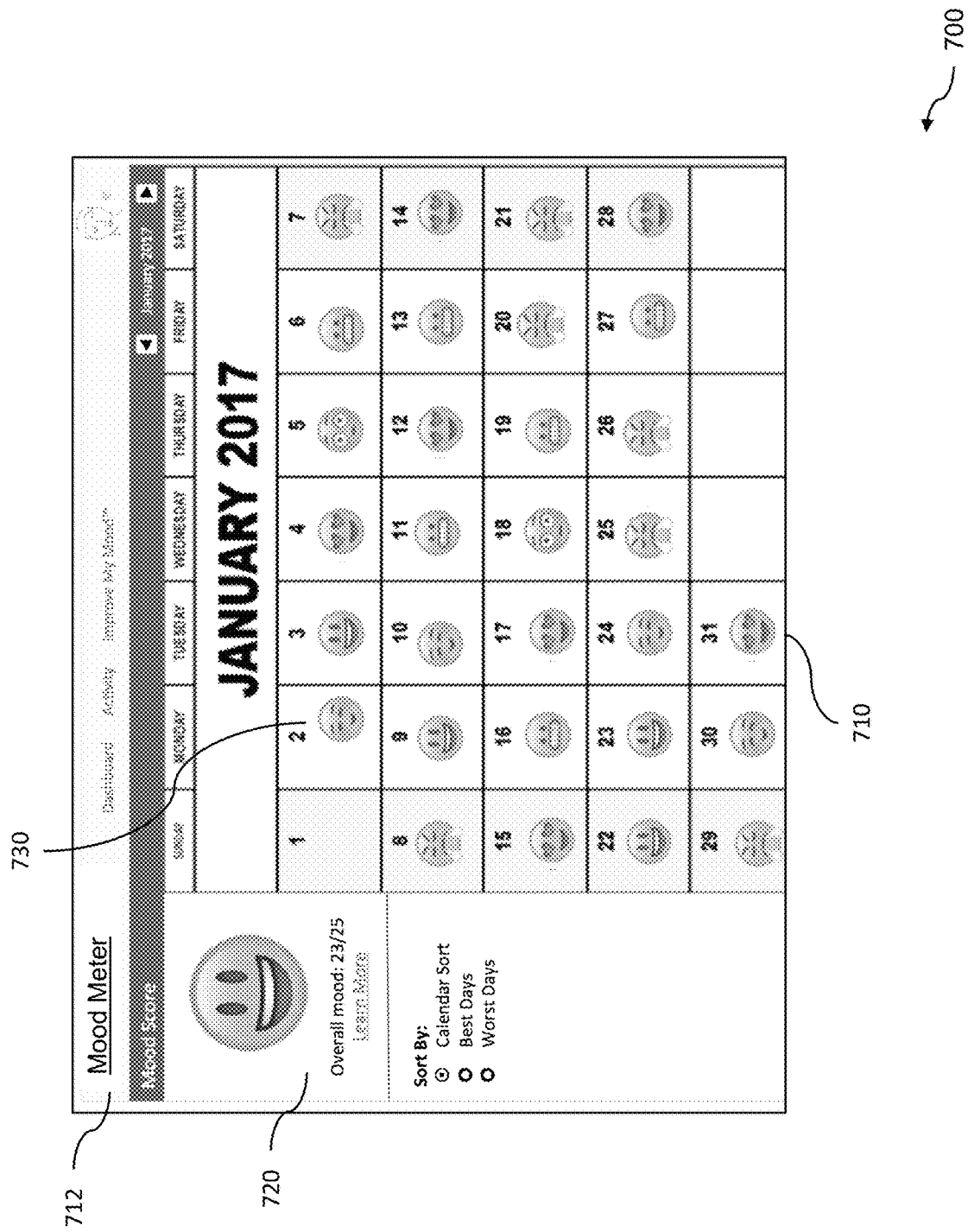
FIG. 7 shows a calendar displaying mood.

FIG. 7 shows a calendar displaying mood. The calendar displaying mood can be a part of a mood dashboard that can be displayed to an individual. The mood dashboard can be based on image analysis and representation for emotional metric threshold evaluation. Image data, including facial images, is collected at a client device from a user interacting with a media presentation. Processors are used to analyze the image data to extract emotional content. Emotional intensity metrics are determined and stored in a digital storage component. The emotional intensity metrics are coalesced into a summary intensity metric, and the summary intensity metric is represented. The representing can include displaying on a screen. A calendar displaying mood 700 can include displaying a mood dashboard 710 to the individual based on the analyzing. The mood dashboard 710 can include controls 712 that can be used to select display options, to monitor activities, to take steps to improve a mood, to receive suggestions for improving a mood, and so on. The mood dashboard can be used to display the moods of an individual based on cognitive state data including facial data collected over a period of time such as a day, a week, a month, and so on. The calendar of the mood dashboard can display an overall mood 720. The overall mood can be based on comparing the cognitive state data collected from the individual with cognitive state data collected from other individuals. In embodiments, the comparing can provide quantified self-information on cognitive states for the individual. The calendar of the mood dashboard can be sorted using various criteria. The various criteria can include moods across a month, best days of the month, worst days of the month, and so on. One or more emoji 730 can be used to represent an overall mood of the individual for a given day.

Figure 8:
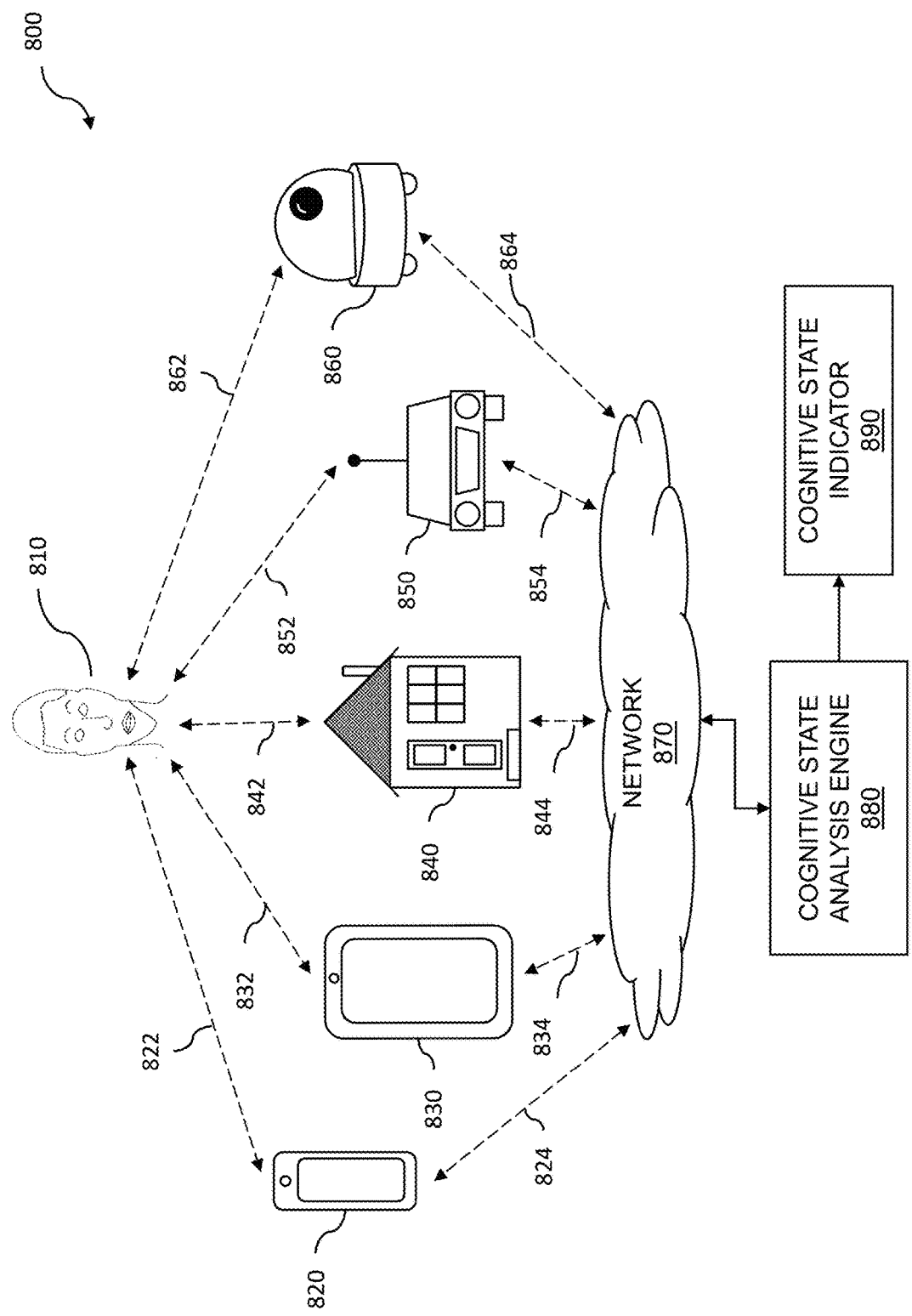
FIG. 8 illustrates image collection including devices and locations.

FIG. 8 illustrates image collection including devices and locations 800. Images can be collected for image analysis and representation for emotional threshold evaluation. Image data and facial images are collected from a user interacting with a media presentation. The collecting occurs at a client device. Processors are used to analyze the image data to extract emotional content. Emotional intensity metrics are determined from the emotional content and are stored in a digital storage component. The emotional intensity metrics are coalesced into a summary emotional intensity metric, and the summary emotional intensity metric is represented. In embodiments, the representing can include displaying the summary emotional intensity metric or the one or more emotional intensity metrics.

Multiple mobile devices, vehicles, and locations, can be used separately or in combination to collect video data or audio data on a user 810. While one person is shown, the video data can be collected on multiple people. A user 810 can be observed as she or he is performing a task, experiencing an event, viewing a media presentation, and so on. The user 810 can be shown one or more media presentations, political presentations, social media, or another form of displayed media. The one or more media presentations can be shown to a plurality of people. The media presentations can be displayed on an electronic display coupled to a client device. The data collected on the user 810 or on a plurality of users can be in the form of one or more videos, video frames, or still images; audio streams or audio clips; etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on.

As noted before, video data can be collected on one or more users in substantially identical or different situations and viewing either a single media presentation or a plurality of presentations. The data collected on the user 810 can be analyzed and viewed for a variety of purposes including expression analysis, mental state analysis, cognitive state analysis, and so on. The electronic display can be on a smartphone 820 as shown, a tablet computer 830, a personal digital assistant, a television, a mobile monitor, or any other type of electronic device. In one embodiment, expression data is collected on a mobile device such as a cell phone or smartphone 820, a tablet computer 830, a laptop computer, or a watch. Thus, the multiple sources can include at least one mobile device, such as a smartphone 820 or a tablet computer 830, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 810, data can be collected in a house 840 using a web camera or the like; in a vehicle 850 using a web camera, client device, etc.; by a social robot 860; and so on.

As the user 810 is monitored, the user 810 might move due to the nature of the task, boredom, discomfort, distractions, or for another reason. As the user moves, the camera with a view of the user's face can be changed. Thus, as an example, if the user 810 is looking in a first direction, the line of sight 822 from the smartphone 820 is able to observe the user's face, but if the user is looking in a second direction, the line of sight 832 from the tablet computer 830 is able to observe the user's face. Furthermore, in other embodiments, if the user is looking in a third direction, the line of sight 842 from a camera in the house 840 is able to observe the user's face, and if the user is looking in a fourth direction, the line of sight 852 from the camera in the vehicle 850 is able to observe the user's face. If the user is looking in a fifth direction, the line of sight 862 from the social robot 860 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 810 can also use a wearable device including a camera for gathering contextual information and/or collecting expression data on other users. Because the user 810 can move her or his head, the facial data can be collected intermittently when she or he is looking in a direction of a camera. In some cases, multiple people can be included in the view from one or more cameras, and some embodiments include filtering out faces of one or more other people to determine whether the user 810 is looking toward a camera. All or some of the expression data can be continuously or sporadically available from the various devices and other devices.

The captured video data can include cognitive content, such as facial expressions, etc., and can be transferred over a network 870. The network can include the Internet or other computer network. The smartphone 820 can share video using a link 824, the tablet computer 830 using a link 834, the house 840 using a link 844, the vehicle 850 using a link 854, and the social robot 860 using a link 864. The links 824, 834, 844, 854, and 864 can be wired, wireless, and hybrid links. The captured video data, including facial expressions, can be analyzed on a cognitive state analysis engine 880, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the cognitive state analysis engine can be processed by a cognitive state indicator 890. The cognitive state indicator 890 can indicate cognitive states, mental states, moods, emotions, etc. In embodiments, the cognitive content can include detection of one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 9:
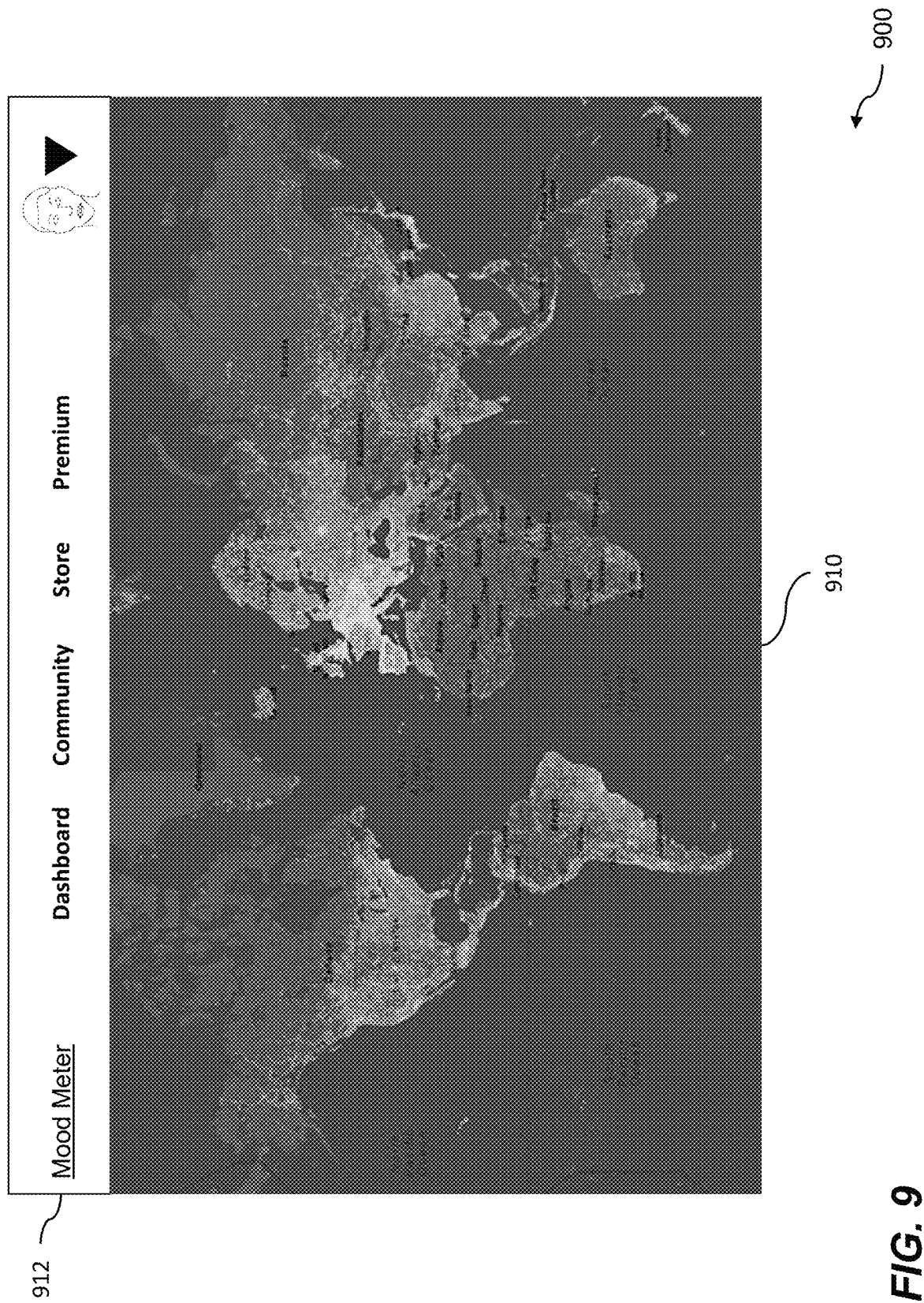
FIG. 9 shows an example world emotional map.

FIG. 9 shows an example world emotional map 900. Image analysis and representation can be performed for emotional metric threshold evaluation. A client device collects image data from a user interacting with a media presentation. The image data that is collected includes facial images of the user. Processors are used to analyze the image data to extract emotional content of the facial images. Emotional intensity metrics are determined and stored in a digital storage component. The emotional intensity metrics are coalesced into a summary intensity metric, and the summary intensity metric is represented. The representing of the summary intensity metric or the other emotional intensity metrics can include generating a graphical representation of a facial expression, where a threshold value has been met for the facial expression. The graphical representation can be attached to a representation of the media presentation. The emotional content resulting from analysis of images of the user can be aggregated with emotional content resulting from analysis of images from other individuals. The aggregated emotional content can be mapped 910. The map can include a local map, a regional map, a state map, a province map, a country map, a continent map, a hemisphere map, a world map, and the like. The map can include an animated map, a cartoon map, a map of a fictional location, etc. The emotional content can be based on a mental state, a cognitive state, a mood, an emotion type, and so on. In embodiments, the emotion type can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. When the emotional content includes a mood, a mood meter 912 can be used to show how that mood is distributed across the globe. The mood that is distributed can be based on the image data of the individual and from other individuals, where the aggregation can be based on demographics. The demographics can include age, gender, race, nationality, and so on. In embodiments, the emotional content from other individuals that is based on demographics can be used to generate the worldwide emotional map 910.

Figure 10:
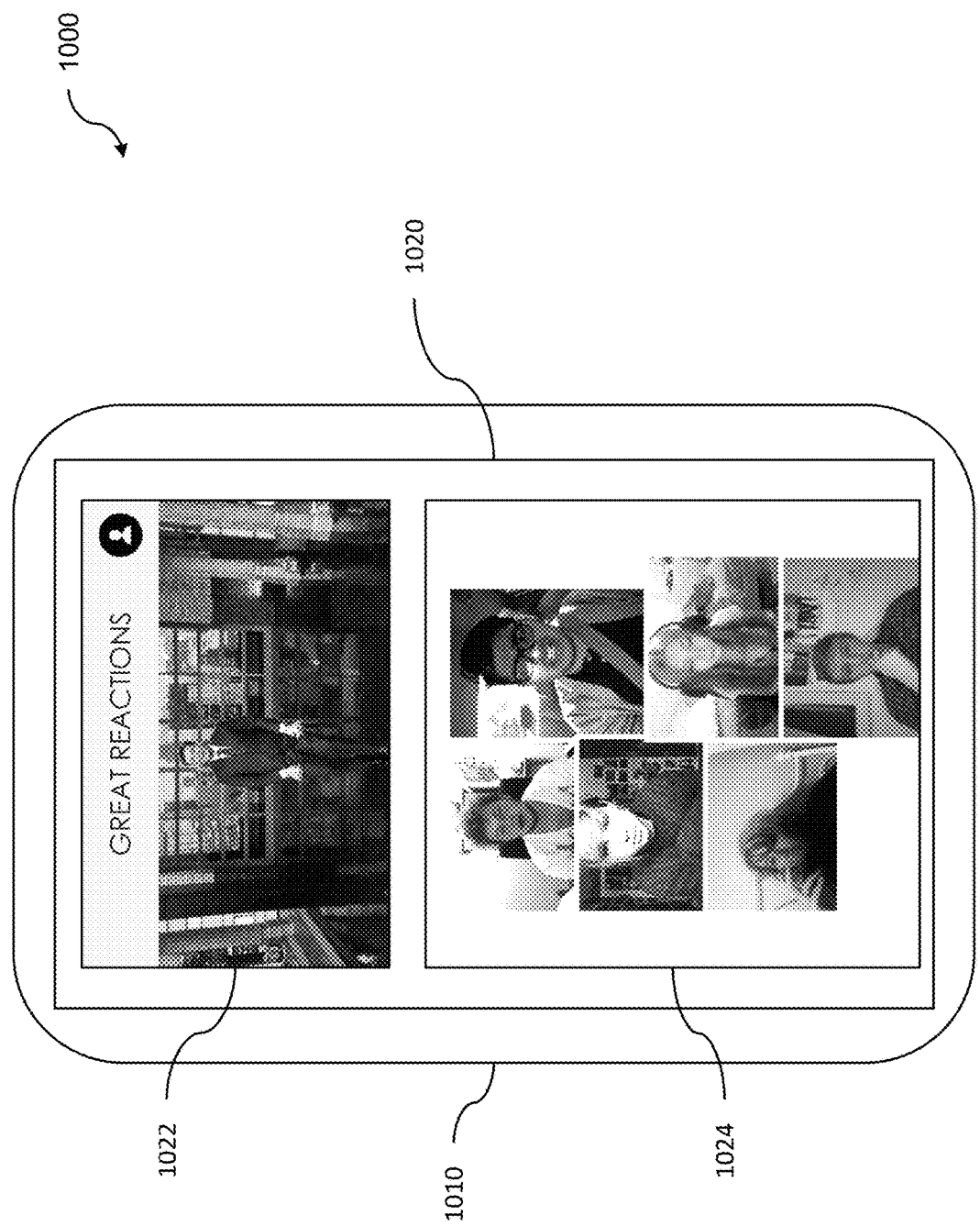
FIG. 10 illustrates reactions to a video.

FIG. 10 illustrates reactions to a video 1000. The reactions to a video can be based on image analysis and representation for emotional metric threshold evaluation. Image data and facial images are collected from a user interacting with a media presentation. Processors are used to analyze the image data to extract emotional content. Emotional intensity metrics are determined from the emotional content and are retained in storage components. The emotional intensity metrics are coalesced into a summary emotional intensity metric, which is represented. A client device 1010 or other device can be used to display 1020 a variety of information. The information that is displayed can include a media presentation 1022, images of reactions of various users 1024, and so on. The media presentation 1022 can include a variety of content including news and information, an advertisement, a political message, education or instructional material, music, a television program, a movie, social sharing, and so on. The reactions 1024 can include reactions of various users to the media presentation 1022. The reactions can include sharing such as social sharing. The social sharing can be accomplished by the users installing and using an app. The app can include opting-in for sharing of the reactions. The reactions can include self-images ("selfies") of the users of the app as those users react to the media presentation.

Figure 11:
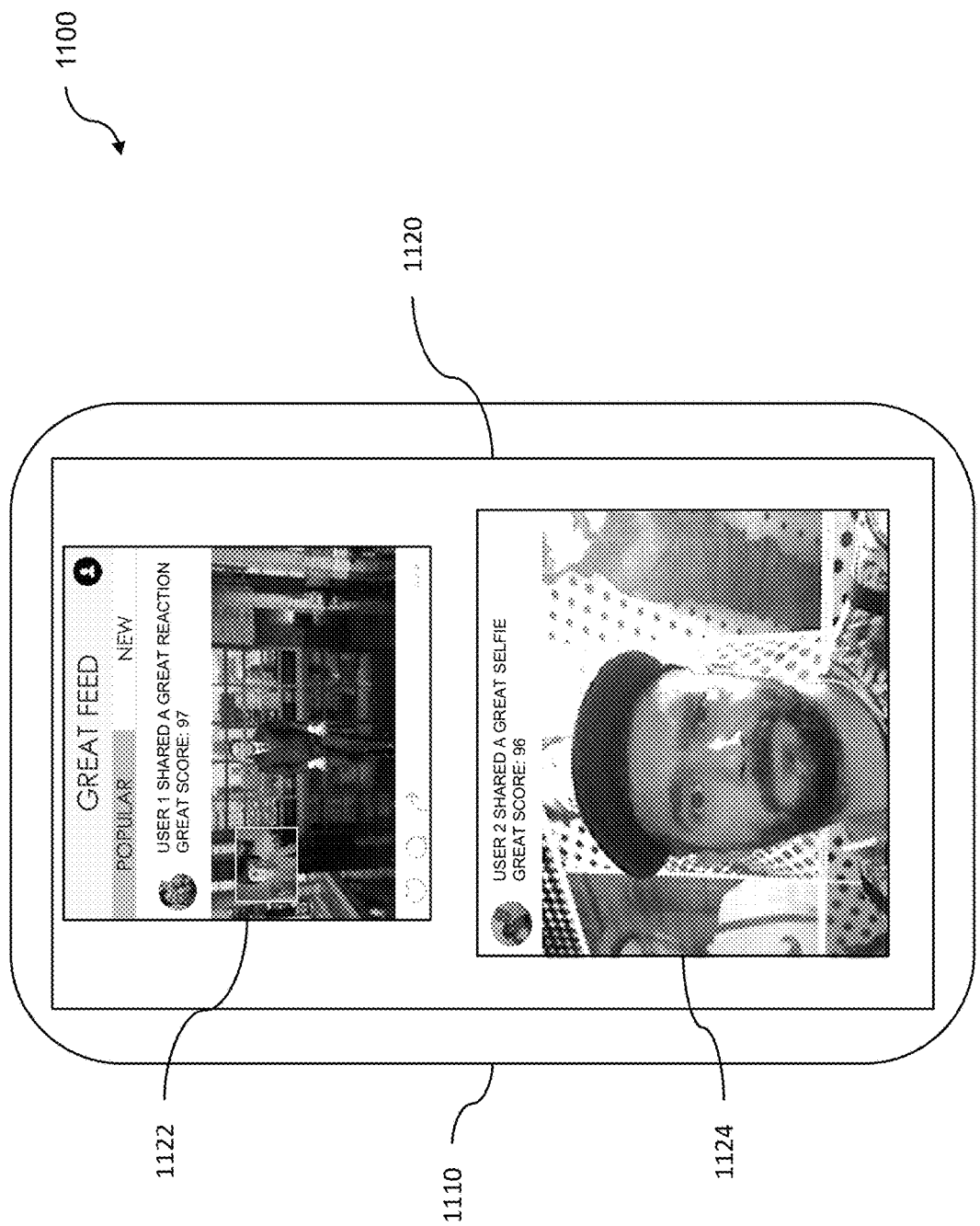
FIG. 11 shows reactions and self-images.

FIG. 11 shows reactions and self-images. Reactions and self-images 1100 can include image analysis and representation for emotional metric threshold evaluation. Image data and facial images are collected from a user interacting with a media presentation. Processors are used to analyze the image data to extract emotional content. Emotional intensity metrics are determined from the emotional content, and the emotional intensity metrics are retained in storage components. The emotional intensity metrics are coalesced into a summary emotional intensity metric, and the summary emotional intensity metric is represented. Reactions and self-images ("selfies") can be displayed on a client device 1110 or other device such as a display with a line of sight to the user. The client device 1110 can include a display 1120 on which a media presentation 1122 and one or more self-images 1124 can be rendered. The media presentation can include social video, video, a video segment, a video frame, a still image, social audio, an audio clip, and so on. The self-image 1124 can include an image of a user who has downloaded an app and opted-in to social sharing using the app. The self-image can be a favorite image shared by the user, an image voted on by other users of the app, and so on. The self-image can include an emoji chosen by the user or that represents the user. The self-image can include an emoticon, a cartoon, and the like. In embodiments, the audio data can include speech, where the speech can include speech data collected from the user, provided by the user, etc. The audio data can include non-speech vocalizations, where the non-speech vocalizations can include audio resulting from the user reacting to the media presentation. In embodiments, the non-speech vocalizations can include grunts, yelps, squeals, snoring, sighs, laughter, filled pauses, unfilled pauses, or yawns.

Figure 12:
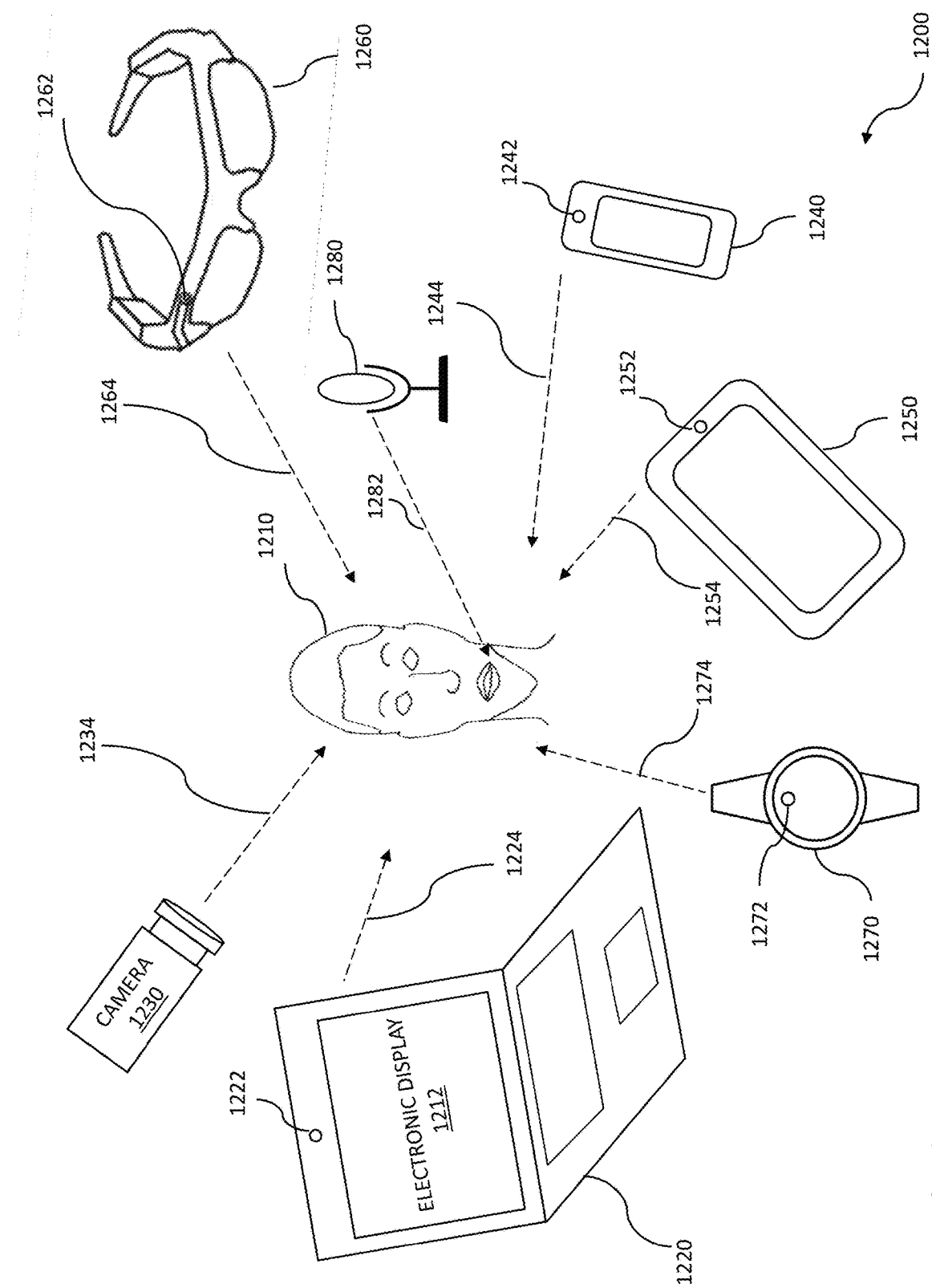
FIG. 12 is a diagram showing image and audio collection including multiple mobile devices.

FIG. 12 is a diagram showing image and audio collection including multiple mobile devices. The collected images can be analyzed and represented for emotional metric threshold evaluation. Image data and facial images are collected from a user interacting with a media presentation. Processors are used to analyze the image data to extract emotional content. Emotional intensity metrics are determined from the emotional content, and the emotional intensity metrics are retained in storage components. The emotional intensity metrics are coalesced into a summary emotional intensity metric, and the summary emotional intensity metric is represented. While one person is shown, in practice the video data or audio data on any number of people can be collected. In the diagram 1200, the multiple mobile devices can be used separately or in combination to collect video data, audio data, physiological data, or some or all of video data, audio data, and physiological data, on a user 1210. While one person is shown, the video data, audio data, or physiological data can be collected on multiple people. A user 1210 can be observed as she or he is performing a task, experiencing an event, viewing a media presentation, and so on. The user 1210 can be shown one or more media presentations, political presentations, social media, or another form of displayed media. The one or more media presentations can be shown to a plurality of people. The media presentations can be displayed on an electronic display 1212 or another display. The data collected on the user 1210 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 1210 can be analyzed and viewed for a variety of purposes including expression analysis, cognitive state analysis, mental state analysis, emotional state analysis, and so on. The electronic display 1212 can be on a laptop computer 1220 as shown, a tablet computer 1250, a cell phone 1240, a television, a mobile monitor, or any other type of electronic device. In one embodiment, video data including expression data is collected on a mobile device such as a cell phone 1240, a tablet computer 1250, a laptop computer 1220, or a watch 1270. Similarly, the audio data including speech data and non-speech vocalizations can be collected on one or more of the mobile devices. Thus, the multiple sources can include at least one mobile device, such as a phone 1240 or a tablet 1250, or a wearable device such as a watch 1270 or glasses 1260. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 1222, a phone camera 1242, a tablet camera 1252, a wearable camera 1262, and a mobile camera 1230. A wearable camera can comprise various camera devices, such as a watch camera 1272. Sources of audio data 1282 can include a microphone 1280.

As the user 1210 is monitored, the user might move due to the nature of the task, boredom, discomfort, distractions, or for another reason. As the user moves, the camera with a view of the user's face can be changed. Thus, as an example, if the user is looking in a first direction, the line of sight 1224 from the webcam 1222 is able to observe the user's face, but if the user is looking in a second direction, the line of sight 1234 from the mobile camera 1230 is able to observe the user's face. Furthermore, in other embodiments, if the user is looking in a third direction, the line of sight 1244 from the phone camera 1242 is able to observe the user's face, and if the user is looking in a fourth direction, the line of sight 1254 from the tablet camera 1252 is able to observe the user's face. If the user is looking in a fifth direction, the line of sight 1264 from the wearable camera 1262, which can be a device such as the glasses 1260 shown and can be worn by another user or an observer, is able to observe the user's face. If the user is looking in a sixth direction, the line of sight 1274 from the wearable watch-type device 1270, with a camera 1272 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1210 can also use a wearable device including a camera for gathering contextual information and/or collecting expression data on other users. Because the user 1210 can move her or his head, the facial data can be collected intermittently when she or he is looking in a direction of a camera. In some cases, multiple people can be included in the view from one or more cameras, and some embodiments include filtering out faces of one or more other people to determine whether the user 1210 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 13:
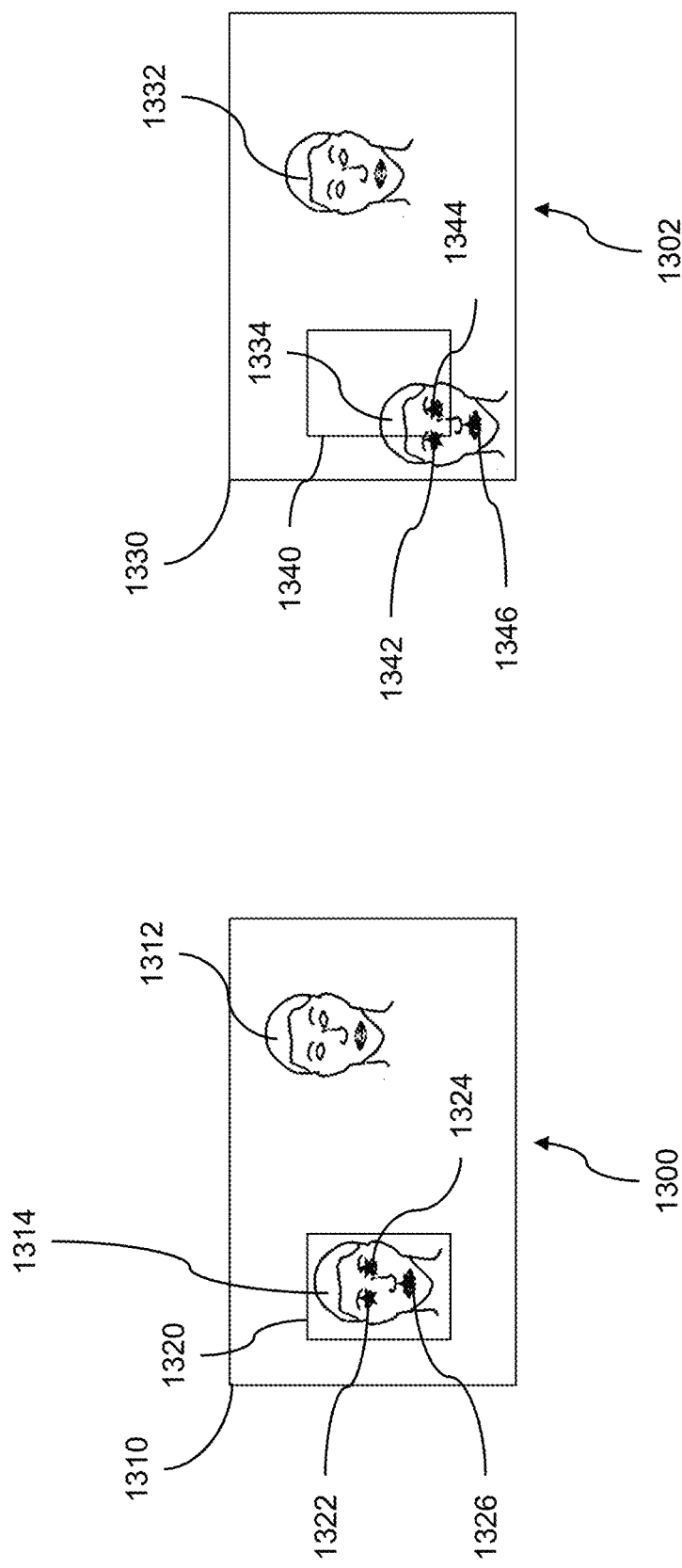
FIG. 13 illustrates feature extraction for multiple faces.

FIG. 13 illustrates feature extraction for multiple faces. The feature extraction for multiple faces can be performed for faces that can be detected in multiple images. The collected images can be analyzed for representation of emotional threshold evaluation. Image data, including facial images, is collected from a user interacting with a media presentation. Processors are used to analyze the image data and to extract emotional content. Emotional intensity metrics are determined and retained in a storage component. The emotional intensity metrics are coalesced into a summary intensity metric, which is represented. The representation can include attaching a graphical illustration to a representation of the media presentation. The representation can be displayed on a screen.

The feature extraction for multiple faces can be performed for faces detected in multiple images. In embodiments, the features of multiple faces are extracted for evaluating cognitive states. Features of a face or a plurality of faces can be extracted from collected video data. The feature extraction can be performed by analysis, by using one or more processors, by using one or more video collection devices, and by using a server. The analysis device can be used to perform face detection for a second face, as well as to perform facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, referred to as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; of detecting the one or more faces in one or more videos; of detecting facial features and landmarks; and so on. The observations can be analyzed based on one or more of a set of quantifiable properties. The properties can be described as features, and explanatory variables involving various data types can include numerical (integer-valued, real-valued), ordinal, categorical, and so on. Some classifiers can be based on a comparison between an observation and prior observations and can also be based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, etc. Algorithms for classification can be implemented using a variety of techniques, including neural networks, kernel estimation, support vector machines, use of quadratic surfaces, and so on. Classification can be used in many application areas such as computer vision and speech and handwriting recognition. Classification can be used for biometric identification of one or more people in a single frame or in multiple frames of one or more videos.

Returning to FIG. 13, the detection of the first face, the second face, and multiple faces can include identifying facial landmarks, generating a bounding box, and predicting a bounding box and landmarks for a next frame, where the next frame can be one of a plurality of frames of a video containing faces. A first video frame 1300 includes a frame boundary 1310, a first face 1312, and a second face 1314. The video frame 1300 also includes a bounding box 1320. Facial landmarks can be generated for the first face 1312. Face detection can be performed to initialize a second set of locations for a second set of facial landmarks for a second face within the video. Facial landmarks in the video frame 1300 can include the facial landmarks 1322, 1324, and 1326. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 1320. Bounding boxes can also be estimated for one or more other faces within the boundary 1310. The bounding box can be refined, as can the one or more facial landmarks. The refining of the second set of locations for the second set of facial landmarks can be based on localized information around the second set of facial landmarks. The bounding box 1320 and the facial landmarks 1322, 1324, and 1326 can be used to estimate future locations for the second set of locations for the second set of facial landmarks in a future video frame from the first video frame.

A second video frame 1302 is also shown. The second video frame 1302 includes a frame boundary 1330, a first face 1332, and a second face 1334. The second video frame 1302 also includes a bounding box 1340 and the facial landmarks, or points, 1342, 1344, and 1346. In other embodiments, multiple facial landmarks are generated and used for facial tracking of the two or more faces of a video frame, such as the shown second video frame 1302. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 1340 can be estimated, where the estimating can be based on the location of the generated bounding box 1320 shown in the first video frame 1300. The three facial points shown, facial points, or landmarks, 1342, 1344, and 1346, might lie within the bounding box 1340 or might not lie partially or completely within the bounding box 1340. For instance, the second face 1334 might have moved between the first video frame 1300 and the second video frame 1302. Based on the accuracy of the estimating of the bounding box 1340, a new estimation can be determined for a third, future frame from the video, and so on. The evaluation can be performed, all or in part, using semiconductor-based logic.

Figure 14:
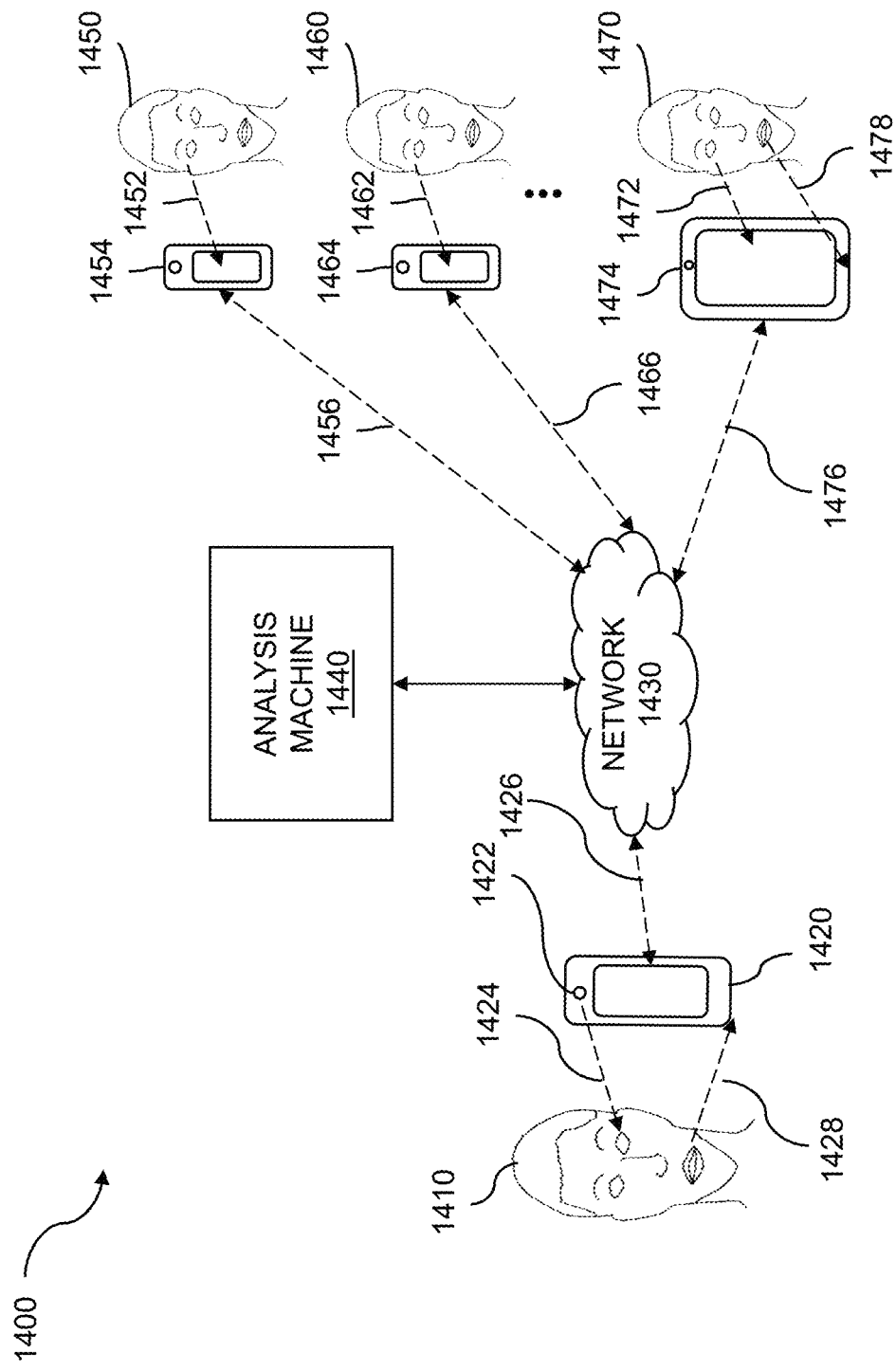
FIG. 14 shows live streaming of social video and audio.

FIG. 14 shows live streaming of social video and audio. The live streaming of social video and social audio can be performed for image analysis and representation for emotional metric threshold evaluation. The live streaming can include emotional content, cognitive state data, image data, facial data, speech data, audio data, etc. The live streaming can include people as they interact with a media presentation, the Internet, a social networking application, and so on. A video and audio of a person or people can be transmitted via live streaming. Image data and facial images are collected from a user interacting with a media presentation. Processors are used to analyze the image data and media presentation, and to extract emotional content of the viewer. Emotional intensity metrics are determined from the emotional content, and the emotional intensity metrics are retained in storage components. The emotional intensity metrics are coalesced into a summary emotional intensity metric, and the summary emotional intensity metric is represented.

The live streaming 1400 and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1400 shows a user 1410 broadcasting a video live stream and an audio live stream to one or more people as shown by a first person 1450, a second person 1460, and a third person 1470. A portable, network-enabled, electronic device 1420 can be coupled to a front-facing camera 1422. The portable electronic device 1420 can be a smartphone, a PDA, a tablet, a laptop computer, and so on. The camera 1422 coupled to the device 1420 can have a line-of-sight view 1424 to the user 1410 and can capture video of the user 1410. The portable electronic device 1420 can be coupled to a microphone (not shown). The microphone can capture voice data 1428 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1440 using a network link 1426 to the Internet 1430. The network link can be a wireless link, a wired link, and so on. The recommendation engine 1440 can recommend to the user 1410 an app and/or platform that can be supported by the server and can be used to provide a video live stream, an audio live stream, or both a video live stream and an audio live stream to one or more followers of the user 1410.

In the example 1400, the user 1410 has three followers: a first person 1450, a second person 1460, and a third person 1470. Each follower has a line-of-sight view to a video screen on a portable, networked electronic device. In other embodiments, one or more followers follow the user 1410 using any other networked electronic device, including a computer. In the example 1400, a first person 1450 has a line-of-sight view 1452 to the video screen of a device 1454; a second person 1460 has a line-of-sight view 1462 to the video screen of a device 1464, and a third person 1470 has a line-of-sight view 1472 to the video screen of a device 1474. The device 1474 can also capture audio data 1478 from the third person 1470. The portable electronic devices 1454, 1464, and 1474 can each be a smartphone, a PDA, a tablet, and so on. Each portable device can receive the video stream and the audio stream being broadcast by the user 1410 through the Internet 1430 using the app and/or platform that can be recommended by the recommendation engine 1440. The device 1454 can receive a video stream and the audio stream using the network link 1456, the device 1464 can receive a video stream and the audio stream using the network link 1466, the device 1474 can receive a video stream and the audio stream using the network link 1476, and so on. The network link can be a wireless link, a wired link, a hybrid link, and so on. Depending on the app and/or platform that can be recommended by the recommendation engine 1440, one or more followers, such as the followers shown 1450, 1460, and 1470, can reply to, comment on, or otherwise provide feedback to the user 1410 using their respective devices 1454, 1464, and 1474.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose additional obstacles to analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 15:
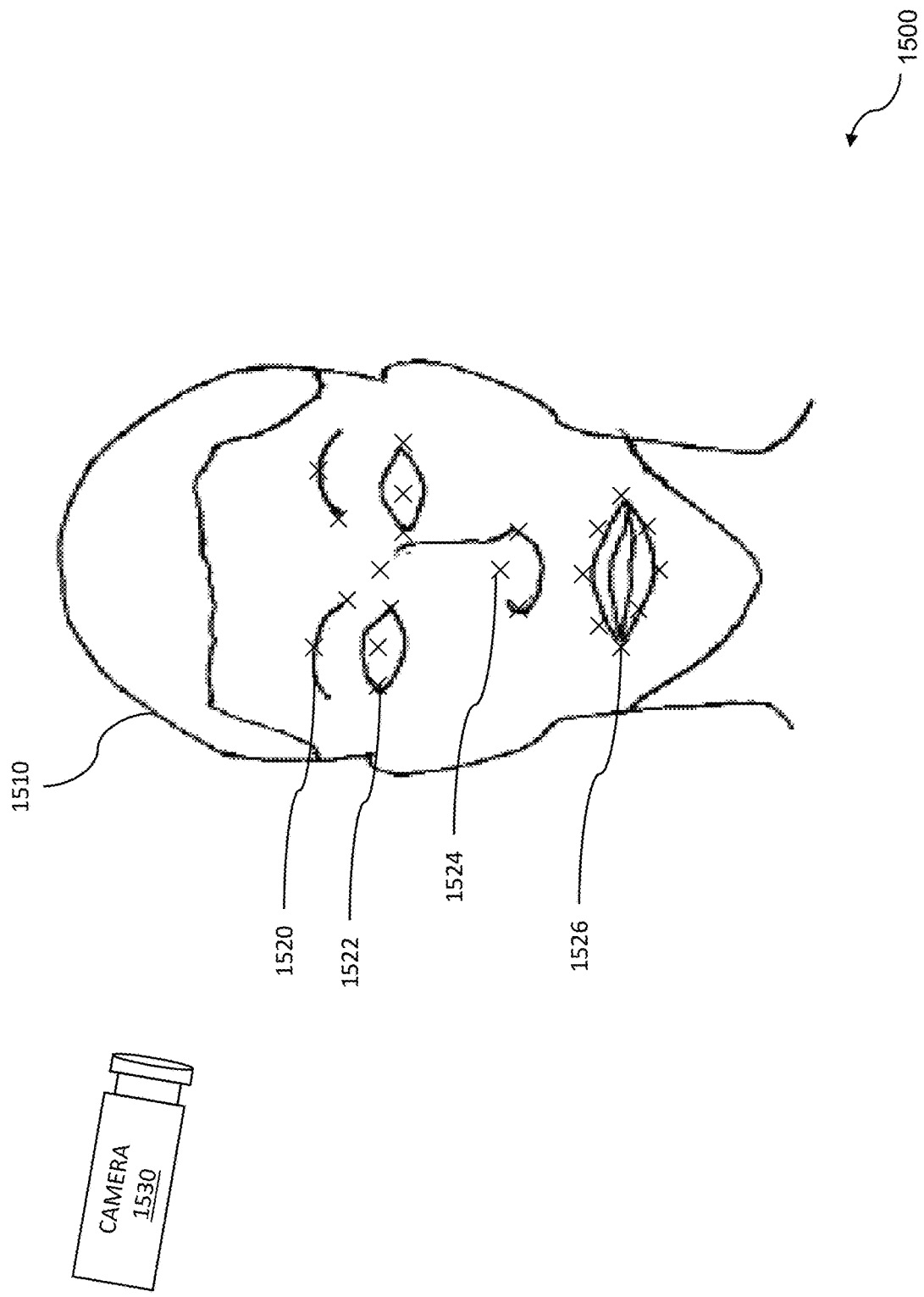
FIG. 15 shows example facial data collection including landmarks.

FIG. 15 shows example facial data collection including landmarks. The collecting of facial data including landmarks can be performed for image analysis and representation for emotional metric threshold evaluation. The facial data including landmarks can include people as they interact with a media presentation, a computer network such as the Internet, a social media site or portal, etc. In the example 1500, facial data including facial landmarks can be collected using a variety of electronic hardware and software techniques. The collecting of facial data including landmarks can be based on enabling an app by an individual. Image data, including facial images, is collected from a user interacting with a media presentation. Processors are used to analyze the image data and the media presentation to extract emotional content. Emotional intensity metrics are determined and retained in a storage component. The emotional intensity metrics are coalesced into a summary intensity metric, and the summary intensity metric is displayed on a screen. A face 1510 can be observed using a camera 1530 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a smartphone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 1530 relative to the face 1510, the number of cameras used, the illumination of the face, etc. In some cases, if the face 1510 is poorly lit or over-exposed (e.g. in an area of bright light), the processing of the facial data to identify facial landmarks might be rendered problematic. In another example, the camera 1530 being positioned to the side of the person might prevent capture of the full face. Other artifacts can degrade the capture of facial data. For example, the person's hair, vision devices (e.g. glasses, an eye patch, and eye coverings), jewelry, and clothing can partially or completely occlude or obscure the person's face. Data relating to various facial landmarks can include a variety of facial features. The facial features can comprise an eyebrow 1520, an outer eye edge 1522, a nose 1524, a corner of a mouth 1526, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 16:
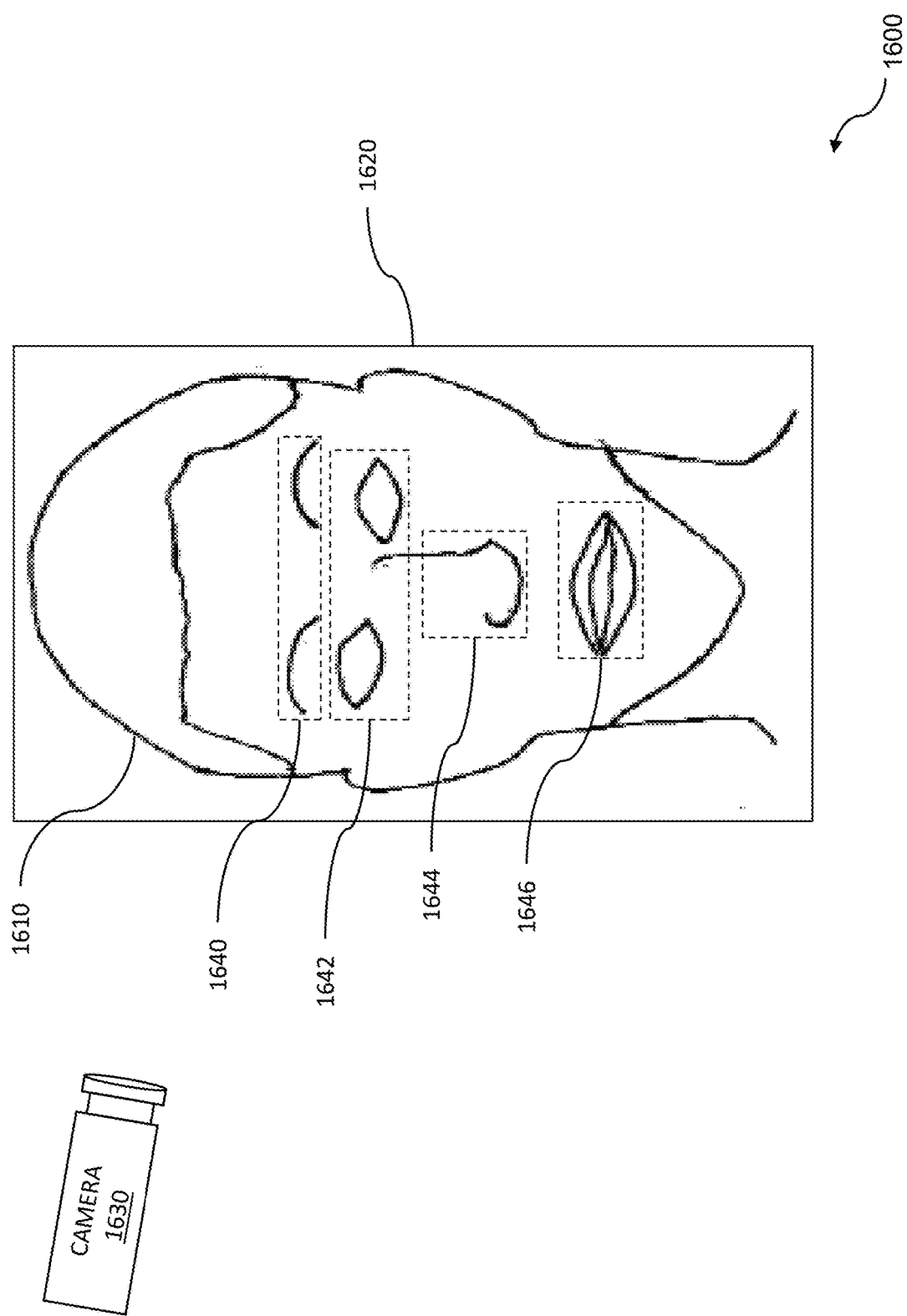
FIG. 16 shows example facial data collection including regions.

FIG. 16 shows example facial data collection including regions. The collecting of facial data including regions can be performed for image analysis and representation for emotional metric threshold evaluation. Image data and facial images are collected from a user interacting with a media presentation. Processors are used to analyze the image data and media presentation, and to extract emotional content. Emotional intensity metrics are determined from the emotional content, and the emotional intensity metrics are retained in storage components. The emotional intensity metrics are coalesced into a summary emotional intensity metric, and the summary emotional intensity metric is represented.

The facial data including regions can be collected from people as they interact with a media presentation, a computer network such as the internet, a website such as a social media site, and so on. Various regions of a face can be identified and used for a variety of purposes including facial recognition, facial analysis, and so on. Facial analysis can be used to determine, predict, estimate, etc. cognitive states, emotions, and so on, of a person from whom facial data can be collected. The one or more emotions that can be determined by the analysis can be represented by an image, a figure, an icon, etc. The representative icon can include an emoji. One or more emoji can be used to represent a cognitive state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji.

In the example 1600, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1610 can be observed using a camera 1630, a sensor, a combination of cameras and/or sensors, and so on. The camera 1630 can be used to collect facial data that can be used to determine if a face is present in an image. When a face is present in an image, a bounding box 1620 can be placed around the face. Placement of the bounding box around the face can be based on detection of facial landmarks. The camera 1630 can be used to collect from the bounding box 1620 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a smartphone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1630 relative to the face 1610, the number of cameras and/or sensors used, the illumination of the face, any obstructions to viewing the face, and so on.

The facial regions that can be collected by the camera 1630, sensor, or combination of cameras and/or sensors can include any of a variety of facial features. The facial features that can be included in the facial regions that are collected can include eyebrows 1640, eyes 1642, a nose 1644, a mouth 1646, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1630, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a check. A gradient in a facial region can include values assigned to local skin texture, shading, etc. A gradient can be used to encode, for example, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on edges, boundaries, and so on, of features that can be included in an image. The detection can be based on various types of analysis of the image. The features in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVM), logistic regression, classification trees, and so on. By way of example, consider facial features that can include the eyebrows 1640. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate that the person from whom the facial data can be collected is annoyed, confused, unhappy, and so on. In another example, consider facial features that can include a mouth 1646. One or more classifiers can be used to analyze the facial region that can include the mouth to determine a probability for either a presence or an absence of mouth edges turned up to form a smile. Multiple classifiers can be used to determine one or more facial expressions.

Figure 17:
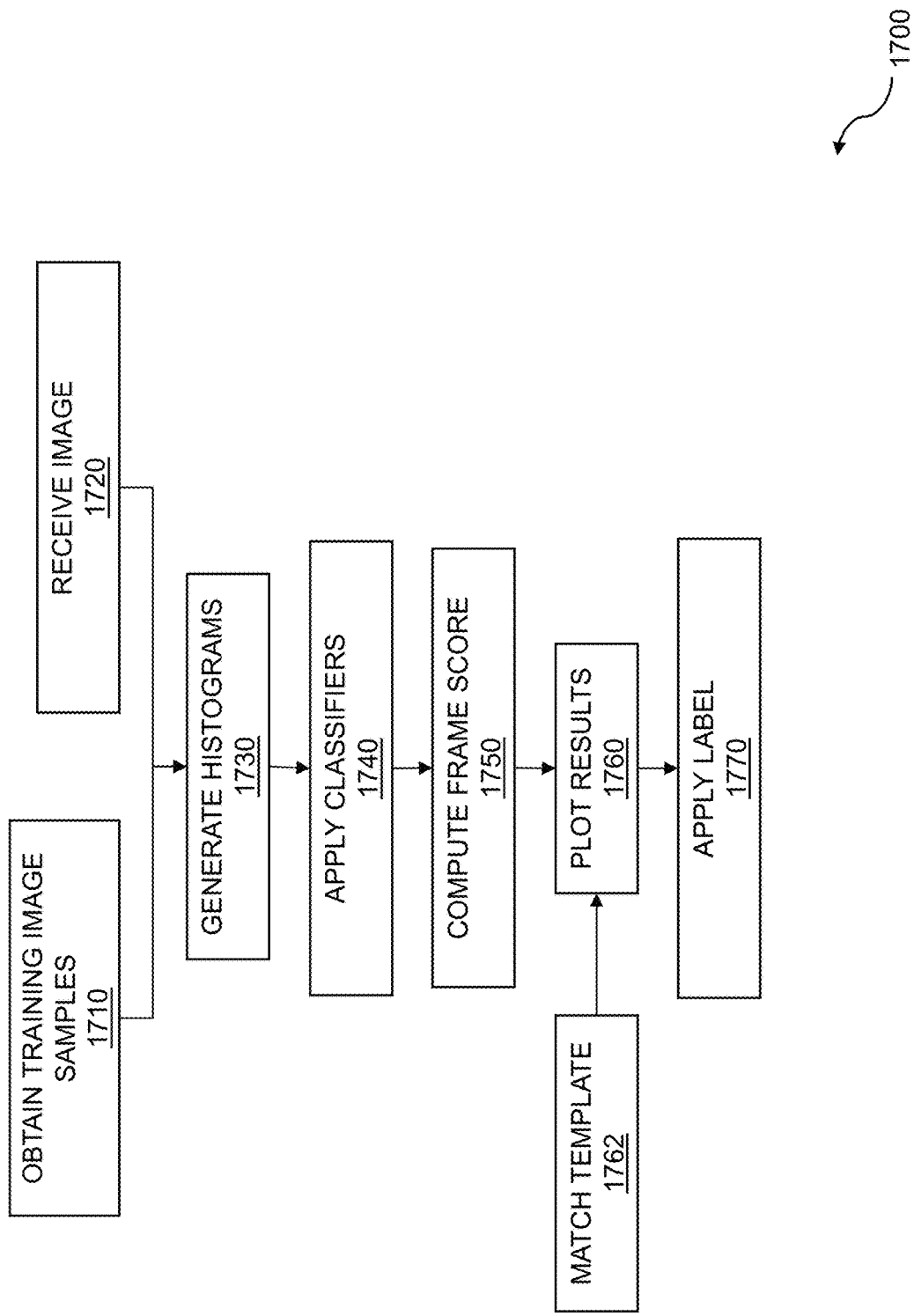
FIG. 17 is a flow diagram for detecting facial expressions.

FIG. 17 is a flow diagram for detecting facial expressions. Image analysis can include detection of facial expressions and can be performed for representation emotional metric threshold evaluation. The facial expressions of people can be detected as they interact with a media presentation, a social network, a webpage, and so on. Image data, including facial images, is collected from a user interacting with a media presentation. Processors are used to analyze the image data and the media presentation to extract emotional content. Emotional intensity metrics are determined and retained in a storage component. The emotional intensity metrics are coalesced into a summary intensity metric, and the summary intensity metric is represented. The flow 1700, or portions thereof, can be implemented in semiconductor logic, can be accomplished using a mobile device, can be accomplished using a server device, and so on. The flow 1700, or portions thereof, can be implemented in semiconductor logic, can be accomplished using a mobile device, can be accomplished using a server device, and so on. The flow 1700 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1700, or portions thereof, can be implemented in semiconductor logic, can be accomplished using a mobile device, can be accomplished using a server device, and so on. The flow 1700 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1700 begins by obtaining training image samples 1710. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1700 continues with receiving an image 1720. The image 1720 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1700 continues with generating histograms 1730 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1700 continues with applying classifiers 1740 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1700 continues with computing a frame score 1750. The score computed for an image, where the image can be a frame from a video, can be used to determine the presence of a facial expression in the image or video frame. The score can be based on one or more versions of the image 1720 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1700 continues with plotting results 1760. The results that are plotted can include one or more scores for one or more frames computed over a given time t. For example, the plotted results can include classifier probability results from analysis of HoGs for a sequence of images and video frames. The plotted results can be matched with a template 1762. The template can be temporal and can be represented by a centered box function or another function. A best fit with one or more templates can be found by computing a minimum error. Other best-fit techniques can include polynomial curve fitting, geometric curve fitting, and so on. The flow 1700 continues with applying a label 1770. The label can be used to indicate that a particular facial expression has been detected in the one or more images or video frames which constitute the image that was received 1720. The label can be used to indicate that any of a range of facial expressions has been detected, including a smile, an asymmetric smile, a frown, and so on. Various steps in the flow 1700 may be changed in order, repeated, omitted, or the like without departing from the disclosed concepts. Various embodiments of the flow 1700 can be included in a computer program product embodied in a non-transitory computer readable medium that includes code executable by one or more processors. Various embodiments of the flow 1700, or portions thereof, can be included on a semiconductor chip and implemented in special purpose logic, programmable logic, and so on.

Figure 18:
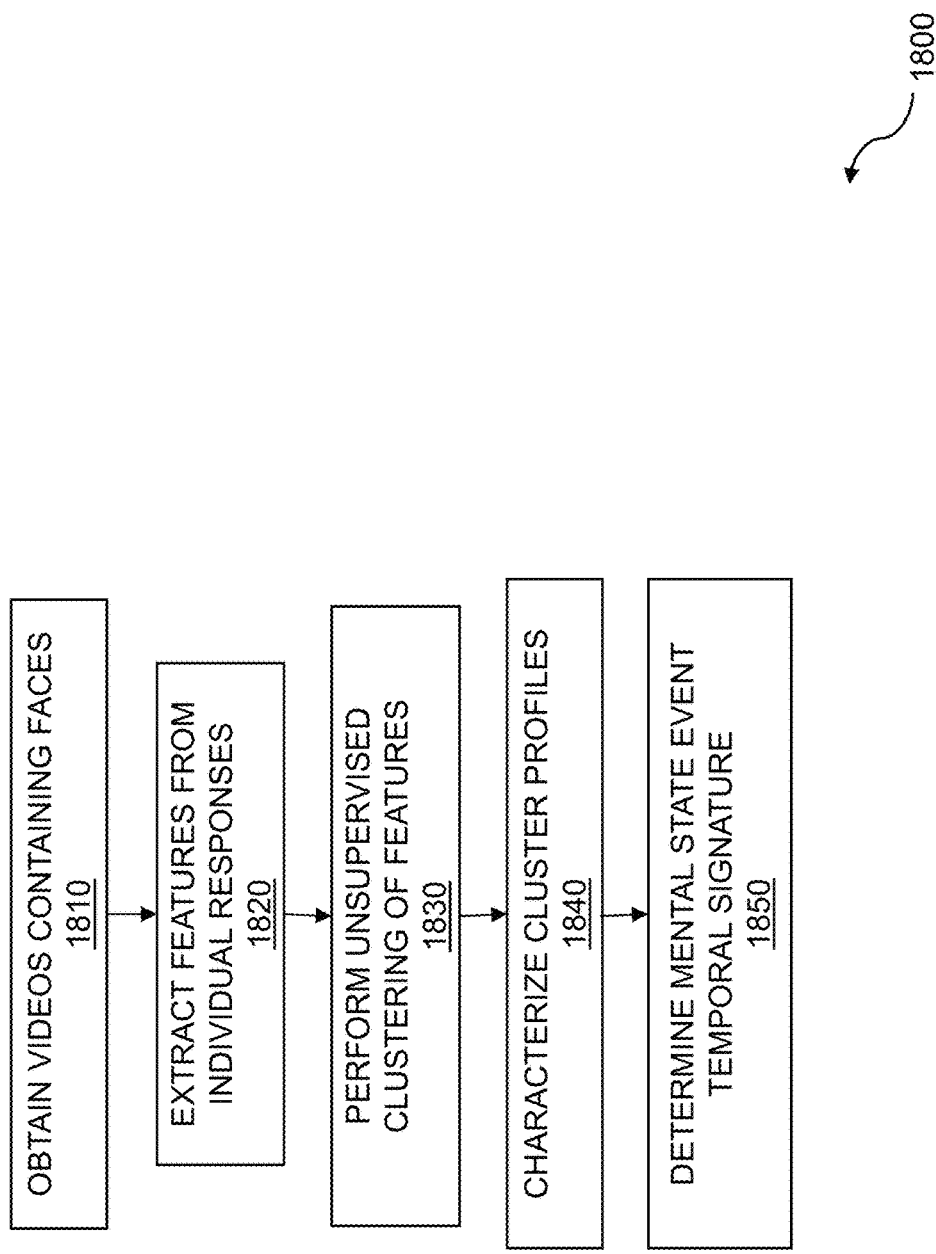
FIG. 18 is a flow diagram for the large-scale clustering of facial events.

FIG. 18 is a flow diagram for the large-scale clustering of facial events. The facial events can be analyzed, where the analysis can include image analysis and representation for emotional threshold evaluation. Image data and facial images are collected from a user interacting with a media presentation. Processors are used to analyze the image data and media presentation, and to extract emotional content. Emotional intensity metrics are determined from the emotional content, and the emotional intensity metrics are retained in storage components. The emotional intensity metrics are coalesced into a summary emotional intensity metric, and the summary emotional intensity metric is represented.

The facial events can be reflective of emotional state events, cognitive state events, mental state events, or moods. The emotional state events can include facial events, speech events, etc. The large-scale clustering of facial events can be performed for data collected from a remote computing device. The facial events can be collected from people as they interact with a medial presentation, with a vehicle, etc. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1800 includes obtaining videos containing faces 1810. The videos can be obtained using one or more cameras, where the cameras can include a webcam coupled to one or more devices employed by the one or more people using the web-based framework. The flow 1800 continues with extracting features from the individual responses 1820. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1800 continues with performing unsupervised clustering of features 1830. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1800 includes characterizing cluster profiles 1840. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1800 can include determining cognitive state event temporal signatures 1850. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1800 may be changed in order, repeated, omitted, or the like without departing from the disclosed concepts. Various embodiments of the flow 1800 can be included in a computer program product embodied in a non-transitory computer readable medium that includes code executable by one or more processors. Various embodiments of the flow 1800, or portions thereof, can be included on a semiconductor chip and implemented in special purpose logic, programmable logic, and so on.

Figure 19:
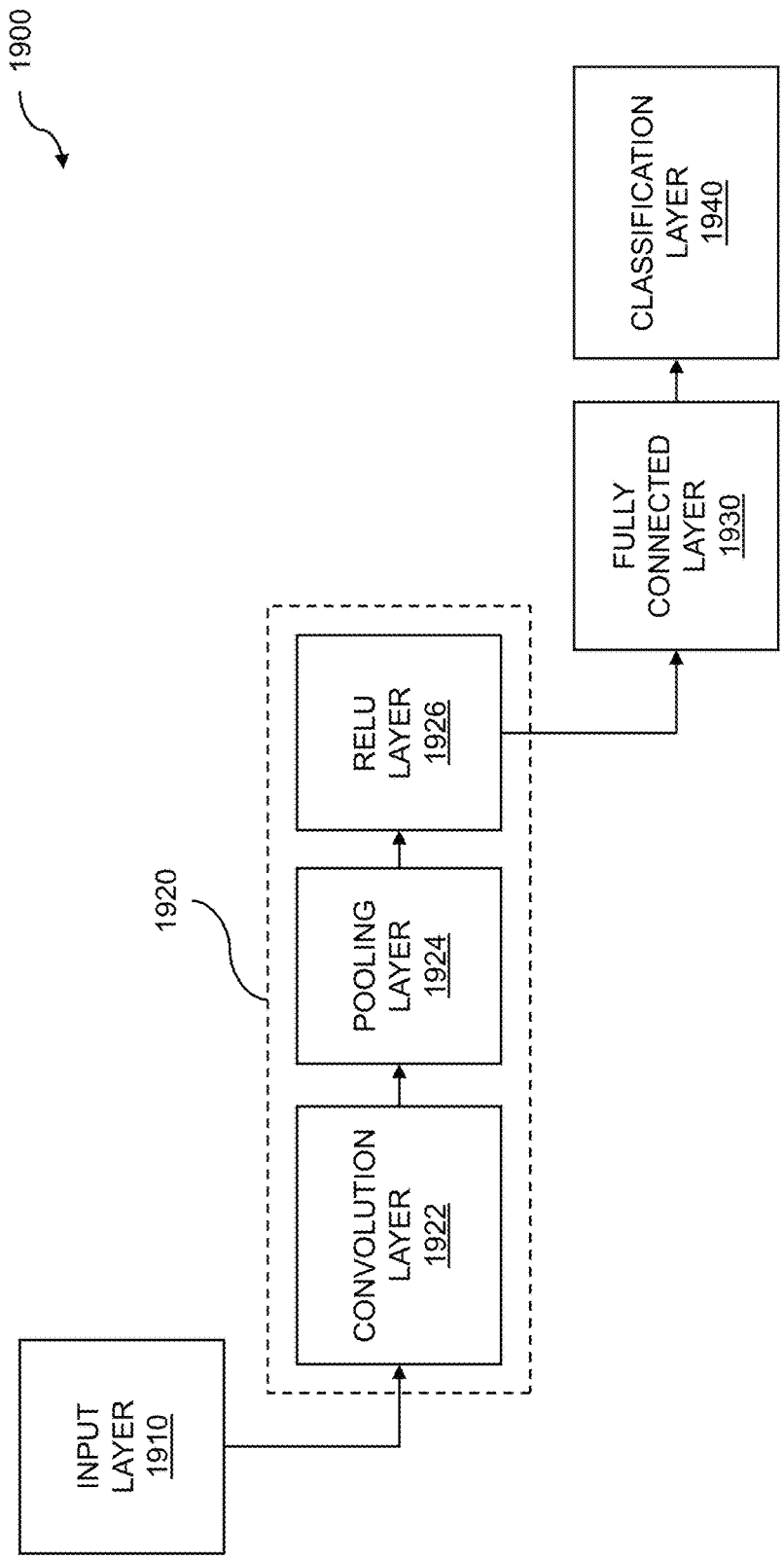
FIG. 19 illustrates a system diagram for deep learning for emotion analysis.

FIG. 19 illustrates a system diagram for deep learning for emotion analysis. Emotion analysis can be based on image analysis and representation for emotional metric threshold evaluation. Emotion analysis is a very complex task. Understanding and evaluating moods, emotions, cognitive states, or mental states, requires a nuanced evaluation of facial expressions or other cues generated by people. Mental state analysis is important to many areas such as research, psychology, business, intelligence, law enforcement, and so on. The understanding of mental states can be used in a variety of fields, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the mental state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the mental state of the audience can be obtained.

Analysis of facial expressions is also a complex undertaking. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be obtained, where the physiological data can be obtained using a camera or other image capture device, without contacting the person or persons. Respiration, heart rate, heart rate variability, perspiration, temperature, and other physiological indicators of mental state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more moods, mental states, emotional states, etc.

The artificial neural network which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of mental state. The last layer of the convolutional neural network can be the final classification layer. The output of the final classification layer can be indicative of the mental states of faces within the images that are provided to the input layer.

Deep networks, including deep convolutional neural networks, can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be feed to next layer. Weights adjust the output of one layer as it is feed to the next layer. When the final layer is reached, the output of the final layer can be a facial expression, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes and on to the output nodes. Additionally, the weights can be updated during a backpropagation process through the multilayered analysis engine.

Returning to the figure, FIG. 19 illustrates a system diagram 1900 for deep learning. The system's deep learning can be accomplished using a convolution neural network or other techniques. The deep learning can accomplish facial recognition and analysis tasks. The network includes an input layer 1910. The input layer 1910 receives image data. The image data can be input in a variety of formats, such as JPEG, TIFF, BMP, and GIF. Compressed image formats can be decompressed into arrays of pixels, wherein each pixel can include an RGB tuple. The input layer 1910 can then perform processing such as identifying boundaries of the face, identifying landmarks of the face, extracting features of the face, and/or rotating a face within the plurality of images.

The network includes a collection of intermediate layers 1920. The multilayered analysis engine can include a convolutional neural network. Thus, the intermediate layers can include a convolution layer 1922. The convolution layer 1922 can include multiple sublayers, including hidden layers within it. The output of the convolution layer 1922 feeds into a pooling layer 1924. The pooling layer 1924 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1924. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1926. The output of the pooling layer 1924 can be input to the RELU layer 1926. In embodiments, the RELU layer implements an activation function such as $f(x)=\max(0,x)$, thus providing an activation with a threshold at zero. In some embodiments, the RELU layer 1926 is a leaky RELU layer. In this case, instead of the activation function providing zero when x<0, a small negative slope is used, resulting in an activation function such as $f(x)=1(x<0)(ax)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1922 and one or more hidden layers, and wherein the multilayered analysis engine can be used for emotional analysis.

The example 1900 includes a fully connected layer 1930. The fully connected layer 1930 processes each pixel/data point from the output of the collection of intermediate layers 1920. The fully connected layer 1930 takes all neurons in the previous layer and connects them to every single neuron it has. The output of the fully connected layer 1930 provides input to a classification layer 1940. The output of the classification layer 1940 provides a facial expression and/or mental state as its output. Thus, a multilayered analysis engine such as the one depicted in FIG. 19 which processes image data using weights, models the way the human visual cortex performs object recognition and learning, and is effective for analysis of image data to infer facial expressions and mental states.

Figure 20:
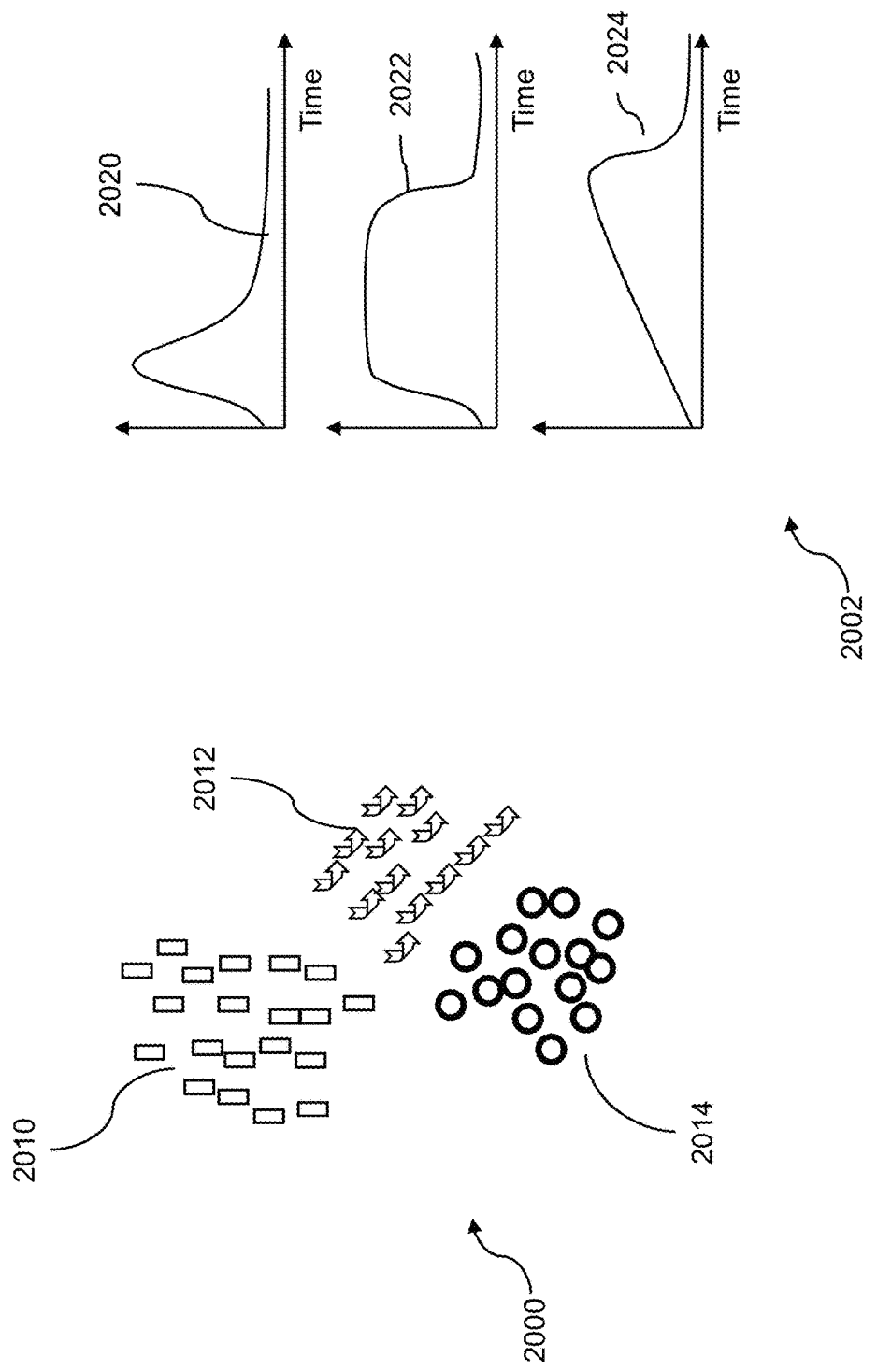
FIG. 20 shows unsupervised clustering of features and characterizations of cluster profiles.

FIG. 20 shows unsupervised clustering of features and characterizations of cluster profiles. The clustering of features and characterizations of cluster profiles can be performed for image analysis and representation for emotional threshold evaluation. Image data and facial images are collected from a user interacting with a media presentation. Processors are used to analyze the image data to extract emotional content. Emotional intensity metrics are determined from the emotional content, and the emotional intensity metrics are retained in storage components. The emotional intensity metrics are coalesced into a summary emotional intensity metric, and the summary emotional intensity metric is represented. Features including samples of facial data can be clustered using unsupervised clustering. Various clusters can be formed which include similar groupings of facial data observations. The example 2000 shows three clusters, clusters 2010, 2012, and 2014. The clusters can be based on video collected from people who have opted-in to video collection. When the data collected is captured using a web-based framework, the data collection can be performed on a grand scale, including hundreds, thousands, or even more participants who can be located in close proximity and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 2002 can be generated based on the clusters that can be formed from unsupervised clustering, with time shown on the x-axis and intensity or frequency shown on the y-axis. The cluster profiles can be based on captured facial data, including facial expressions. The cluster profile 2020 can be based on the cluster 2010, the cluster profile 2022 can be based on the cluster 2012, and the cluster profile 2024 can be based on the cluster 2014. The cluster profiles 2020, 2022, and 2024 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 21A:
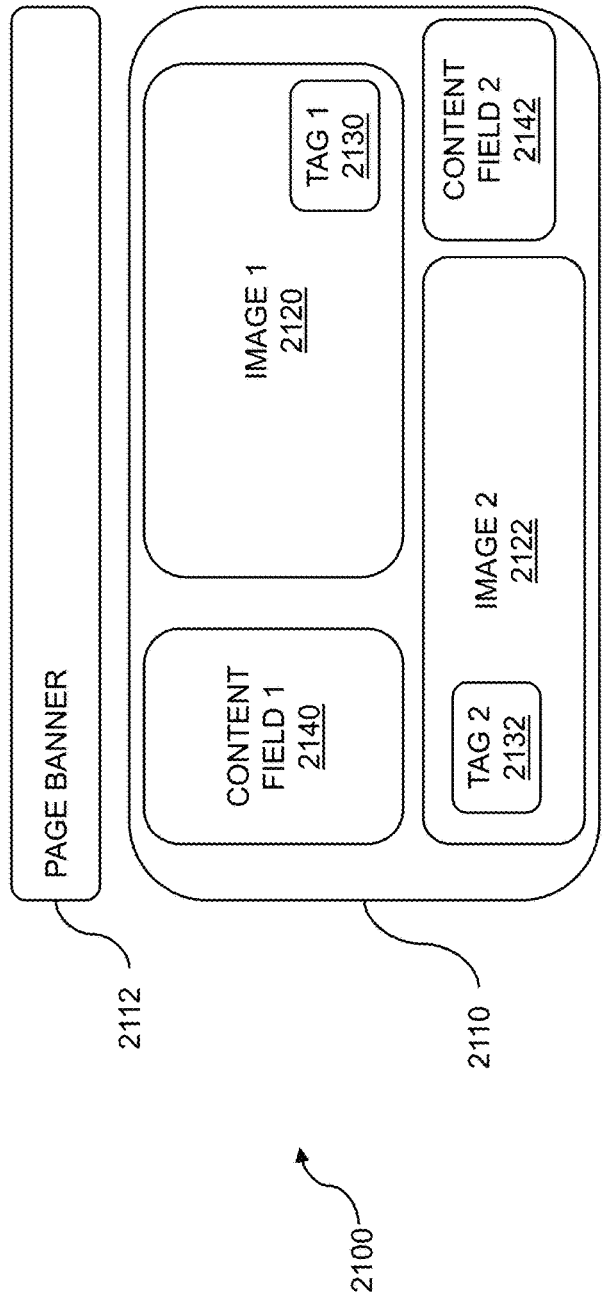
FIG. 21A shows example tags embedded in a webpage.

FIG. 21A shows example tags embedded in a webpage. Tags embedded in a webpage such as a media presentation on a client device can be used to enable image collection. The collected images can include facial images of a user. One or more processors can be used to analyze the image data to extract emotional content of the facial image. Emotional intensity metrics can be determined based on the emotional content, and the emotional intensity metrics can be stored into a digital storage component. The emotional intensity metrics, obtained from the digital storage component, can be coalesced into a summary emotional intensity metric, and the summary emotional intensity metric can be represented.

The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 2100 can include a page body 2110, a page banner 2112, and so on. The page body can include one or more objects, where the objects can include text, images, videos, audio, and so on. The example page body 2110 shown includes a first image, image 1 2120; a second image, image 2 2122; a first content field, content field 1 2140; and a second content field, content field 2 2142. In practice, the page body 2110 can contain multiple images and content fields and can include one or more videos, one or more audio presentations, and so on. The page body can include embedded tags, such as tag 1 2130 and tag 2 2132. In the example shown, tag 1 2130 is embedded in image 1 2120, and tag 2 2132 is embedded in image 2 2122. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 2130, tag 1 2130 can then be invoked. Invoking tag 1 2130 can include enabling a camera coupled to a user's device and capturing one or more images of the user as the user views a media presentation (or digital experience). In a similar manner, when the user mouses over tag 2 2132, tag 2 2132 can be invoked. Invoking tag 2 2132 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 21B:
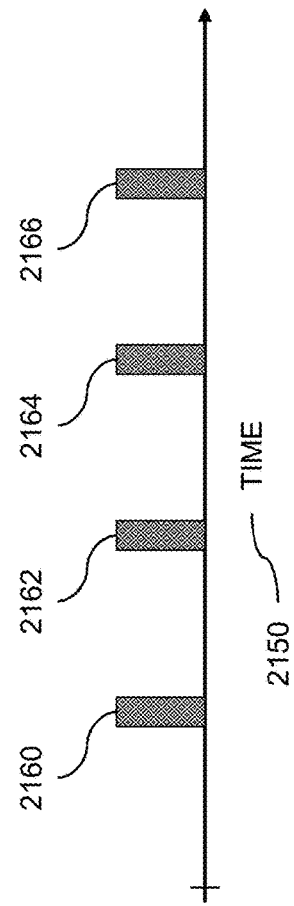
FIG. 21B shows invoking tags to collect images.

FIG. 21B shows invoking tags to collect images. The invoking tags to collect images can be used for image analysis and representation for emotional metric threshold evaluation. The invoking tags to collect images can be used for people as they interact with various content such as media presentations provided to them, including content provided over a computer network such as the Internet. The tags can be related to analysis of emotional state data, mental state data, cognitive state data, etc., for an individual. The tags can be used to analyze the collected image data to extract emotional control of the facial images. Emotional intensity metrics and analyzed and stored based on the emotional content. The emotional intensity metrics, obtained from the digital storage component, are coalesced into a summary emotional intensity metric. The summary emotional intensity metric is represented. The representing can include displaying the representation on a website.

As previously stated, a media presentation can be a video, a webpage, and so on. A video 2102 can include one or more embedded tags, such as a tag 2160, another tag 2162, a third tag 2164, a fourth tag 2166, and so on. In practice, multiple tags can be included in the media presentation. The one or more tags can be invoked during the media presentation. The collection of the invoked tags can occur over time, as represented by a timeline 2150. When a tag is encountered in the media presentation, the tag can be invoked. When the tag 2160 is encountered, invoking the tag can enable a camera coupled to a user device and can capture one or more images of the user viewing the media presentation. Invoking a tag can depend on agreement to opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 2160 neither enables the camera nor captures images of the user during the media presentation. The user can indicate an opt-in for certain types of participation, where opting-in can be dependent on specific content in the media presentation. The user could opt-in to participate in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags embedded in the media presentation that are related to advertisements would not enable the camera when invoked. Various other situations of tag invocation are possible.

The capturing of images, videos, frames from video, audio, etc. of one or more individuals results in the accumulation of substantial quantities of data that is stored for analysis, evaluation, comparison, aggregation, and other purposes. The image and video quality can vary depending on the capabilities of the machine or electronic device that is gathering the image and video data. The video quality can include 15 frames per second (fps), 30 fps, and so on. The data that is received by the one or more individuals, such as content provided by a content provider and delivered over the Internet from a website rendered for the one or more individuals, can also be stored. Further, keystrokes, mouse clicks, invoking tags, and other directed and automatic user actions result in additional data. The result of the capturing of video data, content, user web journey information, and so on, is that the volume of data increases over time.

The data, such as the video data collected from an individual, includes cognitive state data, facial data, and so on. The cognitive state data from the one or more individuals can be analyzed to determine one or more moods, one or more cognitive states, one or more emotional states, etc., for the one or more individuals. The purposes of the analysis can vary and can include determining whether a web site, web content, and so on makes a given individual happy, sad, angry, and so on. Such analysis can compare recently collected data to data collected in the past, where the past can be earlier in the day, a previous day, an earlier week, last year, etc. This "data telescoping" can be useful to both the individual consumer of web content and to the content provider of the web and other content. The data telescoping can be used to recommend and/or direct an individual to a website that makes her or him happy, to avoid websites that induce anger, and so on. Additionally, the data telescoping can be used by a content provider to send to an individual content in which that individual demonstrates interest, to refrain from sending content that makes the individual angry, etc.

The value of the stored data changes over time. Current data can have the highest value and relevance and can be stored in its entirety at a micro level. As the data ages, the typical trend is for the data to become less useful for such actions as predicting a current cognitive or emotional state in an individual, determining which content to provide, and so on. Various techniques can be used to determine what to do with the aging data. For example, after a week, the cognitive state data for an individual may be less relevant for determining current cognitive or emotional state, but can still maintain relevance for making comparisons of moods, emotions, cognitive states, determining trends, and so on. Over time, the data can be aggregated to time intervals. Such time intervals can include aggregating to one second intervals after a week, aggregating to the minute after a month, aggregating to the hour after a year, etc. The aggregation of data can be based on different techniques. One technique for data aggregation can include overall levels identified in the data such as whether the individual is happier, angrier, more confused, etc., when visiting a web site or other content conduit. Another technique for data aggregation can include events such as numbers of smiles, eyebrow raises, scowls, etc. Aggregation of the data can also be based on filters used to identify data that should be kept, and other data that should be discarded.

The techniques used for the storage of the data are based on cost of storage, convenience of storage, uses of the data, and so on. Such data "warehousing" typically supports multiple uses of the data. A content provider may want to know the current cognitive and emotional states of an individual in order to provide that individual with content that will make the individual happy. The data storage accessed by the content provider can be fast and "nearby" for ready access immediately. By comparison, data scientists studying the collected data may be satisfied with slower, "farther away" storage. This latter class of storage provides for less expensive storage of larger quantities of data than does the former class of storage.

Figure 22:
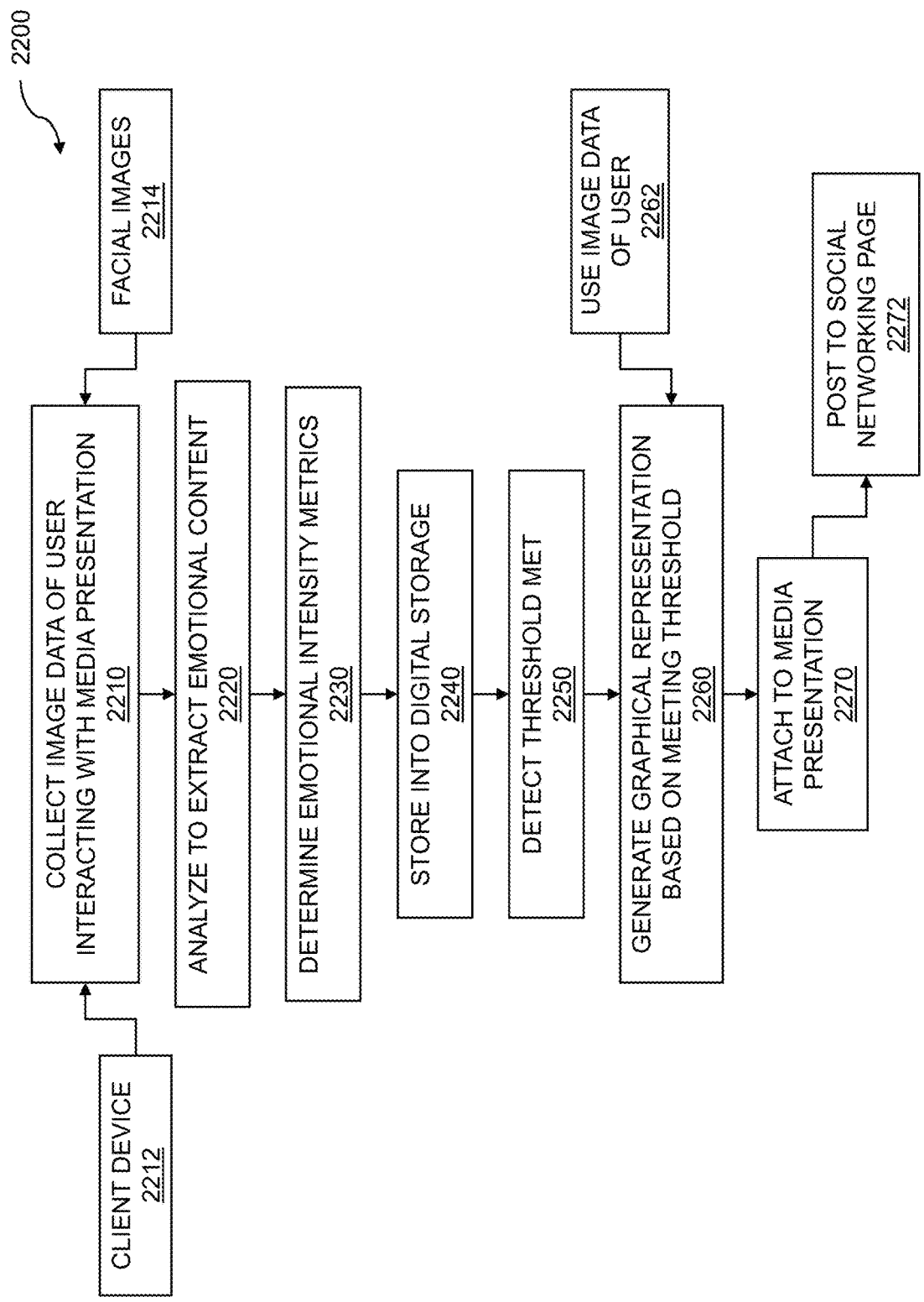
FIG. 22 is a flow diagram for a looping GIF based on a self-image.

FIG. 22 is a flow diagram for a looping GIF based on a self-image. Graphics interchange format (GIF) files can include images and short animations. GIF files including short animations can be posted on webpages, uploaded to social media, or used in other social sharing contexts. GIF animations can include sequences of video frames, images including self-images such as "selfies", and the like. The GIF animations can also include a video loop of a sequence of self-images. A flow for looping a GIF file based on self-images 2200 is shown. The flow 2200 includes collecting, at a client device, image data of a user interacting with a media presentation 2210, where the image data can include the user's facial images. In embodiments, the image data can include buffered image frames. The image frames can include video frames extracted from the collected image data. The buffer that includes the buffered image frames can be a "running buffer" where the running buffer stores a quantity of image frames, a time duration of image frames, etc. The quantity or time duration can remain constant as the window of the buffer "runs" through the video data that was collected. In embodiments, the image frames can transpire over two seconds of time. The media presentation can include a video, a video clip, an advertisement, educational material, a political presentation, and the like. In embodiments, media presentation can include a webpage, a social networking page, or a shared social video channel. The facial images 2214 include self-images, which are frequently referred to as "selfies." The self-images can be collected from a user as the user interacts with a client device 2212, where the client device can be a handheld device such as a smartphone, personal digital assistant (PDA), tablet, etc.; a laptop computer; a desktop computer; a smart television; etc. The self-images can be collected with a camera or cameras coupled to one or more of the client devices. In embodiments, the media presentation includes a webpage, a social networking page, or a shared social video channel. The flow 2200 includes analyzing, using one or more processors, the image data to extract emotional content 2220 of the facial images. The collected self-images can be analyzed to detect emotional content. The emotional content can include one or more emotions. The emotions can be detected in a facial expression located in the self-images. An emotion can include an emotion type, where the emotion type can include one or more of the following: sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, or mirth.

The flow 2200 includes determining one or more emotional intensity metrics 2230 based on the emotional content. The emotional intensity metrics measure the intensity, duration, and frequency of an emotion by assigning a percentage or comparative value to it. The flow 2200 includes storing the emotional intensity metrics into a digital storage 2240 component. The digital storage component can be coupled to the client device used for the collection of image data including facial images. The digital storage component can be coupled to a local server or other processing device, a remote server, a distributed server, a cloud server, a mesh server, etc. The stored emotional intensity metrics can be used for analysis. The flow 2200 includes detecting that a threshold value has been met 2250 by the emotional intensity metrics. The emotional intensity metric threshold can include an intensity of an emotion and can be based on a percentage, a numerical value, a subjective value, or a comparative value. In embodiments, the threshold value can be based on evaluation of facial movements of the user. The threshold value based on facial movements can be based on the facial action coding system (FACS). The intensity of an emotion can include such facial expressions as a strong smile, a deep eyebrow furl, a strong frown, a strong glower, or a pronounced smirk. In embodiments, the threshold value can be based on evaluation of facial movements by a group of users. The group of users may be experiencing the same media presentation. Image data is collected from a group of users and is analyzed for emotional content. An emotion that exceeds a threshold can increase in intensity as the emotion forms, and decrease in intensity as the emotion wanes. The collected self-images from the user can be collated. The collated frames can include frames collected before a given emotion exceeds a threshold and frames collected after the threshold has been initially exceeded. The self-images can be extracted from a running buffer that can contain self-images collected over a period of time. The period of time can include one or more seconds, minutes.

The flow 2200 includes generating a graphical representation 2260 of a facial expression for the user based on the threshold value having been met. The graphical representation can include text, images, a webpage, and so on. In embodiments, the graphical representation can include a video. The video can be generated with the user's image data 2262, a caricature of the user, a cartoon of the user, etc. In embodiments, the graphical representation can include an emoji or an emoticon. The emoji or the emoticon can include a standard, library, or custom emoji or emoticon. The emoji can include an animated emoji. The animated emoji can be assembled from two or more emoji. Similar to the emoji and the animated emoji, the emoticon can include an animated emoticon. The user's image data includes facial images, where the facial images can include self-images. The video can be generated by collating video frames. The video can include image frames extracted from the collected video data, where the frames include image frames from the time period before the threshold value was met. The video frames can be extracted from video data collected from the user both before and after the emotion threshold was exceeded. The series of video frames can include a series of self-images. The video that is generated can include an animation, where the animation can be formed from the series of video frames. The animation can include a graphics interchange format (GIF) animation. The animation can be looped, where the animation plays to the end, then starts again at the beginning of the animation. The number of frames that can be collated into the animation can range from a small number of frames such as 2 or 3 frames, to a larger number of frames such as 10 to 20 frames. Other numbers of frames can also be used.

The flow 2200 includes attaching the graphical representation to a representation of the media presentation 2270. The graphical representation attached to the representation of the media presentation can be rendered on a display device. The display device can include a display coupled to a client device such as a smartphone, a personal digital assistant, a tablet, a laptop computer, or a desktop computer. The display can include other types of electronic displays such as a smart television, a projector, etc. In embodiments, the video can include image frames from the time before the threshold value was met and also includes image frames from the time after the threshold value was met. The graphical representation and the representation of the media presentation can be provided on a social network. The social network can include a plurality of sites, portals, etc. The flow 2200 can further include posting the video to a social networking page 2272. The social networking page can be coupled to any of a variety of social networking applications such as Facebook™, Twitter™, LinkedIn™ Google+™ Instagram™, as Pinterest™. The social networking page can include a count, a tally, a metric, and the like. Further embodiments include incrementing a page metric for the media presentation based on the threshold value having been met. The incremented page metric can include a number of smiles per day, a number of likes, a number of views, etc. In embodiments, the page metric can include a number of likes across multiple users. The number of likes across multiple users can include a number of times that a number of users liked a social networking page, the number of users who met a threshold, etc. In other embodiments, the page metric can include a count for the user having met the threshold value multiple times.

Figure 23:
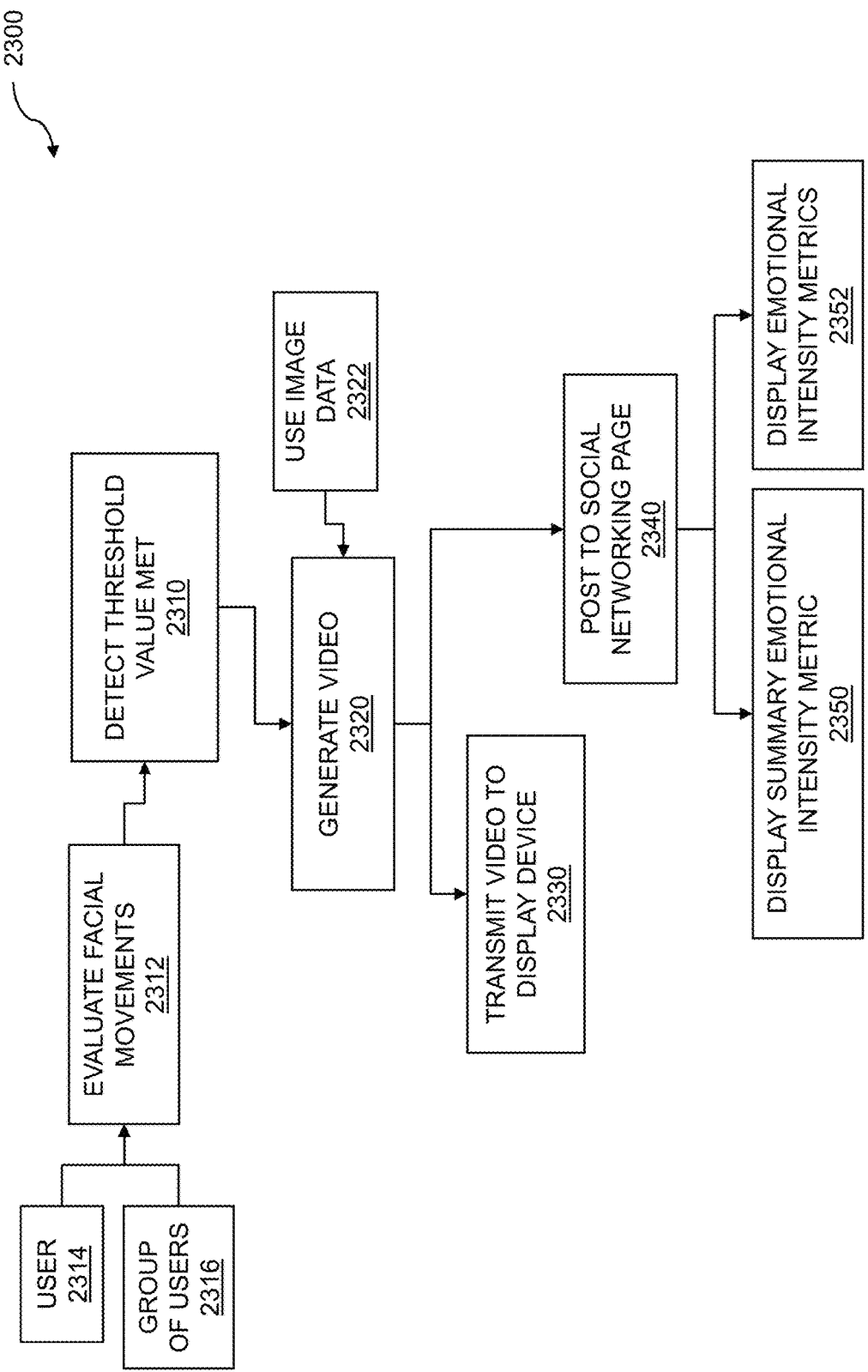
FIG. 23 is a flow diagram for displaying emotional intensity metrics.

FIG. 23 is a flow diagram for displaying emotional intensity metrics. As discussed throughout, one or more emotional intensity metrics can be determined based on emotional content of images collected of a user interacting with a media presentation. The emotional metrics, which can include a number of times that a threshold is exceeded, an intensity of an emotion, a duration of an emotion, and so on, can be determined based on analysis of the collected user images. The collected user images can include facial images of the user. The emotional intensity metrics can be stored in a digital storage component for coalescing into a summary emotional intensity metric, for generating a graphical representation of a facial expression for the user, and the like. The summary emotional intensity metric can be represented, the graphical representation can be attached, and so on.

The flow 2300 includes detecting that a threshold value has been met 2310 by the one or more emotional intensity metrics. Discussed throughout, the one or more emotional intensity metrics can be based on a threshold being exceeded, a number of occurrences, a count of approvals by other users such as "likes", a duration, and so on. In embodiments, the threshold value can be based on evaluation of facial movements 2312 of the user. The facial movements of the user 2314 can include movements of one or more facial muscles. The facial movements of the user can include opening or closing of eyes, winks, nostril flares, movements of one or both ears, movements of the mouth such as smiles, frowns, smirks, grimaces, and the like. More than one facial movement of the user can be evaluated for a threshold value. In embodiments, the threshold value can be based on evaluation of facial movements of a group of users 2316. The group of users may be interacting with a substantially similar media presentation. The group of users may be interacting with the media presentation separately or together (e.g. collocated). The group of users may be sharing a social media page, platform, portal, etc.

The flow 2300 includes generating a video 2320. The video can be captured by a client device or other device. The video can include a video clip, a series of video frames, and so on. The video can be assembled from self-images or "selfies" of a user. The video can be generated using the image data 2322 of the user, based on the video captured by the client device. The video can be generated based on a threshold value having been met. The flow 2300 includes transmitting the video to a display device 2330. The transmitting can include sending the video using a network such as the Internet, an intranet, etc. The transmitting can include wireless techniques such as Wi-Fi, Bluetooth, infrared (IR), and the like. The display device can include a screen coupled to the client device used to collect image data of the user. In embodiments, the video can include image frames from the time before the threshold value was met. For example, the video can include image frames showing the onset of a broad smile.

The flow 2300 includes posting the video to a social networking page 2340. The social networking page can include a page associated with a user, a page associated with a group, and so on. The social networking page can be associated with a social networking site or application, where the social networking site or application can include Facebook™, Google+™ Instagram™, LinkedIn™, Swarm™, Tumblr™, Twitter™, etc. The video can include a representation of the user such as an animated emoji, a GIF, a cartoon, and the time. The video can be based on representing parameters such as emotional intensity metrics. The flow 2300 includes displaying the summary emotional intensity metric 2350 or the one or more emotional intensity metrics 2352. The displaying can include rendering the video, the summary emotional intensity metric, or one or more emotional intensity metrics on a display associated with the client device. The displaying can include rendering the video on a display within a line of sight of the user.

Figure 24:
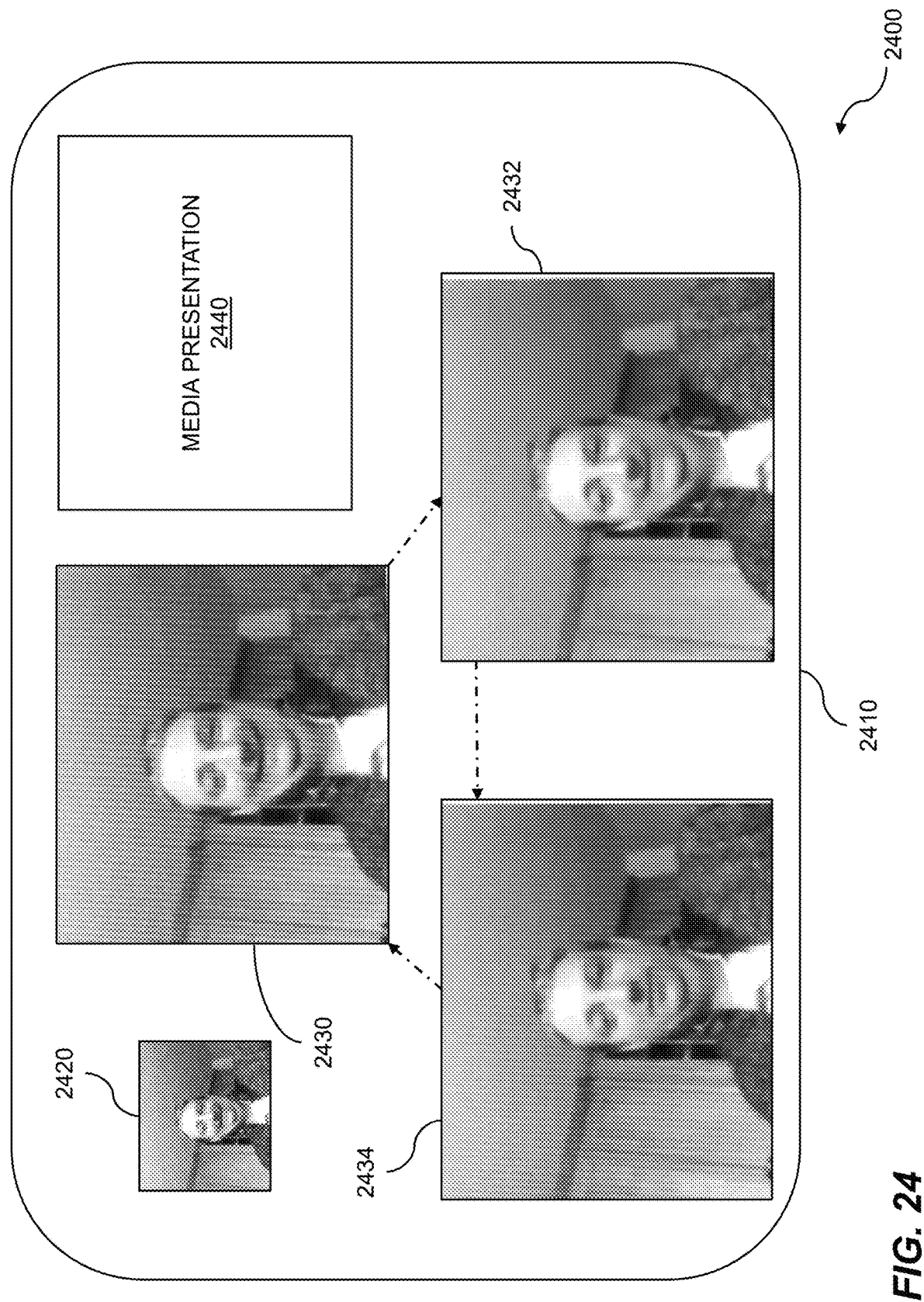
FIG. 24 is an example showing a looping GIF from a self-image.

FIG. 24 is an example showing a looping GIF from a self-image. Animation files, including GIF animation files, can be formed from sequences of self-images. The GIF animation files, which can include 2 or more self-images, can be looped. The looping of the GIF files can occur over a period of time, where the period of time can range from 2 or 3 seconds to longer periods of time. There can be a pause between displays of the GIF animation. The looped GIF animation files can be displayed on a user's electronic device to which the user has a line of sight. An example of a looping GIF animation formed from self-images is shown 2400. The looping GIF animation can be displayed on a screen coupled to an electronic device 2410 such as a smartphone, personal digital assistant (PDA), tablet, laptop computer, desktop computer, or smart television. Other content can be displayed on the screen. In embodiments, the content can include an image of a user 2420, a media presentation 2440 with which the user is interacting, and a looping GIF formed from a sequence of self-images of the user.

A sequence of self-images which can form a looping GIF is shown. The sequence can also include a progression of image frames, where the image frames can be extracted from the image data including facial data of the user. The image frames can be buffered, where the buffer can be a running buffer. The self-images, images, and image frames, etc., can transpire over two seconds of time, or other periods of time. Images can include a first self-image 2430, a second self-image 2432, a third self-image 2434, etc. While three images are shown to represent the sequence of self-images in the animated GIF, other numbers of images can be included. In embodiments, up to ten self-images can be chosen to form the GIF animation. A sequence for displaying the self-images is shown. When an emotion threshold is reached, where the emotion can include joy, anger, surprise, etc., then the GIF animation can be assembled from self-images extracted from a buffer. The images for which an emotional threshold was reached can be chosen based on various criteria. The criteria can include an intensity of the emotion, onset of the emotion, decay of the emotion, and a neutral expression. The GIF animation can be displayed on the screen of the user's device. The GIF animation can be shared socially. Social sharing of the GIF animation can include sharing on a social media platform, a webpage, or a channel.

Figure 25:
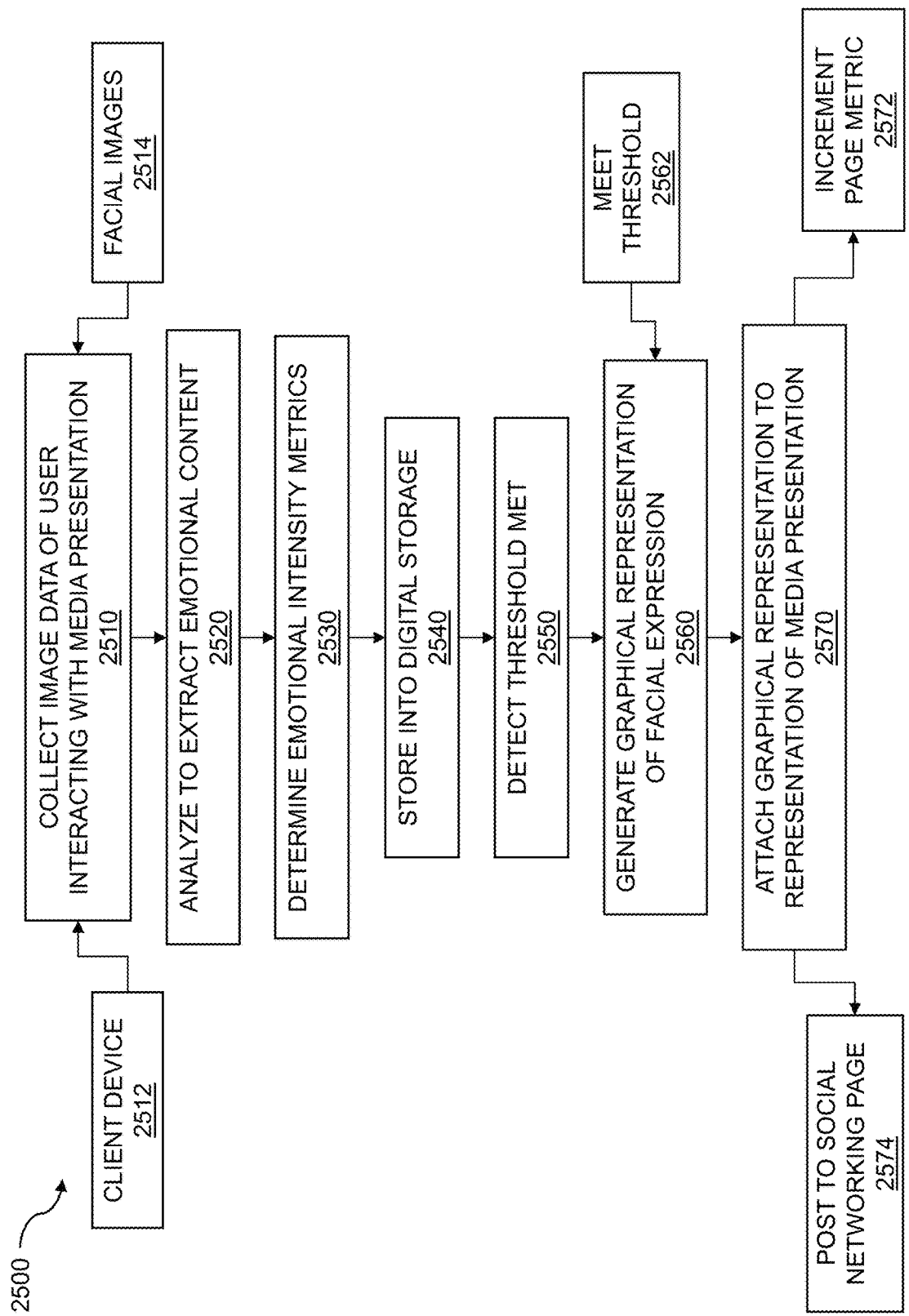
FIG. 25 is a flow diagram for emotion-triggered emoji rendering.

FIG. 25 is a flow diagram for emotion-triggered emoji rendering. Emoji are widely used throughout social media, social sharing, and even communications channels such as short message service (SMS) text, and electronic mail. Emojis can represent a user's moods, emotions, cognitive states, and mental states, as the user interacts with a media presentation. Emojis can be matched to an emotional state of a user. A flow for rendering an emoji which is triggered by a detected user emotion is shown 2500. The flow 2500 includes collecting, at a client device, image data of a user interacting with a media presentation 2510. The image data can be collected using a webcam, a camera or cameras coupled to one or more of the client devices. The image data includes facial images 2514 of the user. The facial images 2514 of the user can include self-images, or "selfies." The self-images can be collected from a user as the user interacts with a client device 2512, where the client devices can include a smartphone, personal digital assistant (PDA), tablet, etc.; a laptop computer; a desktop computer; a smart television; etc. The self-images can be collected using a camera or cameras coupled to one or more of the client devices. The media presentation can include a webpage, a social networking page, or a shared social video channel. The flow 2500 includes analyzing, using one or more processors, the image data to extract emotional content 2520 of the facial images. The image data, collected self-images, etc., can be analyzed to detect emotional content. The emotional content can include one or more emotions detected in the user's facial expressions which are located in the self-images. These emotions include: sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, or mirth.

The flow 2500 includes determining one or more emotional intensity metrics 2530 based on the emotional content. The emotional intensity metrics can be determined using various parameters and can include the intensity, duration and frequency of an emotion. The emotional intensity metrics can include a value, a percentage, and a comparative value. The flow 2500 includes storing the one or more emotional intensity metrics into a digital storage 2540 component. The digital storage component can be situated locally, remotely, or can be distributed. The digital storage component can be coupled to the client device used for the collection of image data including facial images. The digital storage component can be coupled to a local server or other processing device, a remote server, a distributed server, a cloud server, a mesh server, etc. The stored emotional intensity metrics can be used for analysis. The flow 2500 includes detection that a threshold value has been met 2550 by the emotional intensity metrics. The emotional intensity metric threshold can include an intensity value calculated or assigned to an emotion. The emotional intensity metric can be based on a percentage, a numerical value, a subjective value, or a comparative value. The threshold value can be based on evaluation of the user's facial movements. The threshold value based on facial movements can be based on the facial action coding system (FACS). The intensity of an emotion can be measured by a strong smile, a deep eyebrow furl, a strong frown, a strong glower, or a pronounced smirk. The intensity of the emotion can be based on an intensity scoring such as is used by the FACS. The intensity scoring can range from A trace to E maximum. An emotion that can exceed a threshold can increase in intensity during emotion onset, and decrease in intensity during emotion decay. In embodiments, the one or more emotional intensity metrics, obtained from the digital storage component, can be coalesced into a summary emotional intensity metric The flow 2500 includes generating a graphical representation of a user's facial expression 2560 based on the threshold value having been met 2562. In embodiments, graphical representation includes an emoji or an emoticon. The graphical representation can include a cartoon, a graphics interchange format (GIF) file, an animation, etc. Generation of the graphical representation can include more than one emoji, emoticon, cartoon, GIF, animation, etc. When more than one graphical representation is generated, graphical representations can include both static and animated representations. Meeting the threshold can include meeting a value, a subjective value, a relative value, a preassigned value, or a percentage. In other embodiments, the generated a graphical representation of a user's facial expression can be based on the summary emotional intensity metric, described throughout. The flow 2500 includes attaching the graphical representation to a representation of the media presentation 2570. Attaching the graphical representation to the representation of the media presentation can include combining the representations, superimposing the graphical representation on top of the media presentation, or using the graphical representation as a background to the media representation. The graphical representation can be displayed near the representation of the media presentation, such as to the left or right, on the top or bottom, or on a diagonal with respect to the representation of the media presentation. The flow 2500 can further include incrementing a page metric 2572 for the media presentation based on the threshold value having been met. Many instances of a page metric can be imagined such as love, hate, in favor of, opposed to, and so on. In embodiments, the page metric includes a number of likes across multiple users. Similarly, the page metric can include a number of dislikes, loves, hates, amusements, or surprises. In embodiments, the page metric includes a count for the user having met the threshold multiple times. The count can be a minimum, maximum, or average. For example, the count can include the user attaining a smile a specific number of times over a certain time period. Similarly, the threshold can include not getting angry more than a specific number of times over a time period. The time period can be determined by any time period such as an hour, day, week, or month. In embodiments, the graphical representation and the representation of the media presentation can be provided on a social network. The providing on a social network can include posting on a user's social media page 2574, posting on a shared page, or streaming on a video channel.

Figure 26:
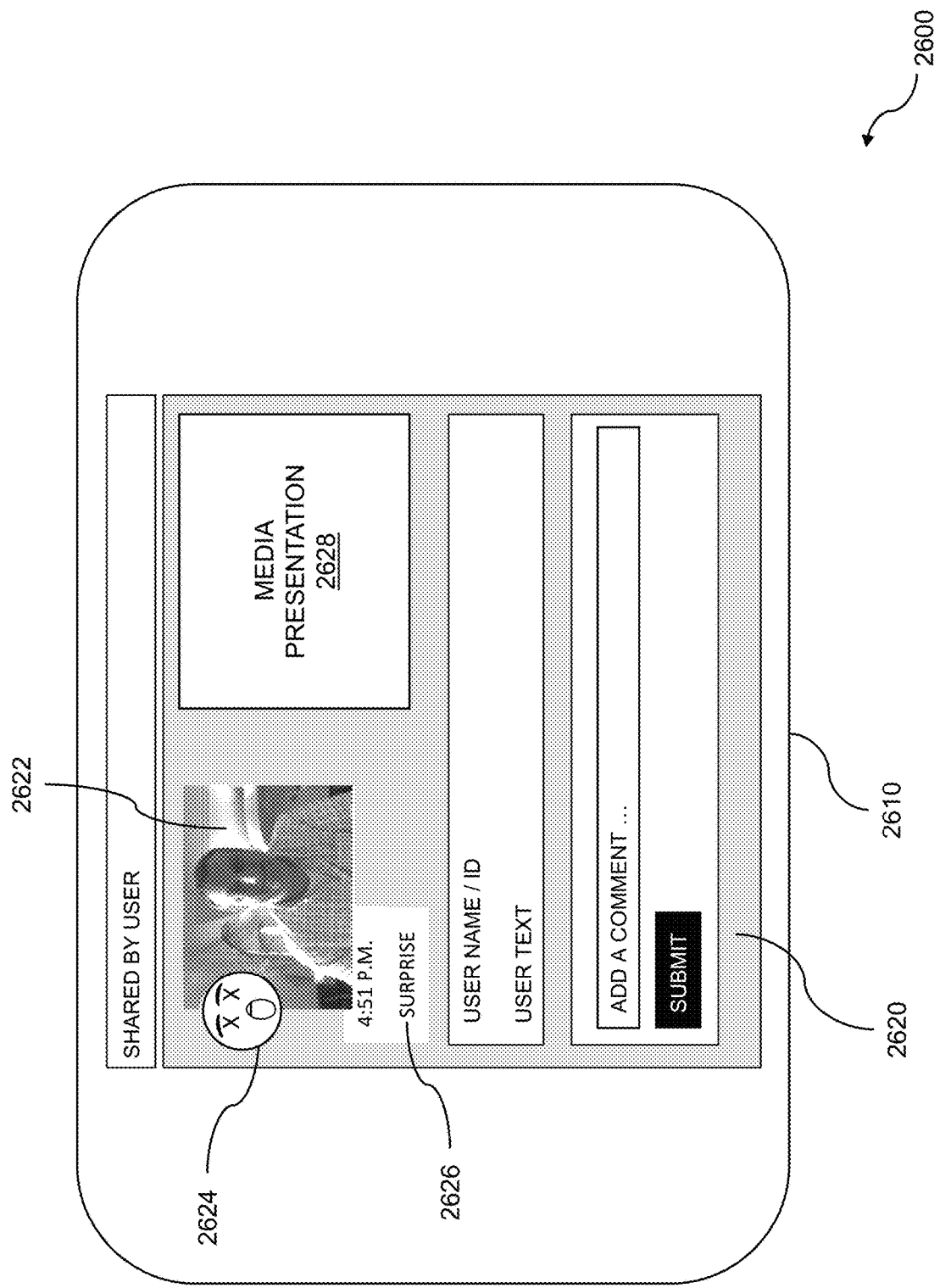
FIG. 26 is an example showing a rendered emoji based on an emotion trigger.

FIG. 26 is an example showing a rendered emoji based on an emotion trigger. A user who is interacting with a media presentation can experience a range of emotions, cognitive states, mental states, moods, and so on. The one or more emotions that the user can experience can be analyzed for parameters such as onset, duration, decay, intensity, and frequency. A given emotion that may be detected can be used to increase the tally of occurrences of that emotion based on the media presentation such as a "like" count. More than one tally or metric relating to the given emotion can be accumulated. In embodiments, the one or more emotional intensity metrics, obtained from the digital storage component, can be coalesced into a summary emotional intensity metric. Based on the detected emotion, a representation of the given emotion can be determined. Further, the summary emotional intensity metric can be represented. The representation can be rendered and displayed along with the media presentation. An example showing a rendered emoji based on an emotion trigger resulting from a media presentation is shown 2600. The content 2620 can be displayed on a screen 2610 coupled to a device such as a smartphone, personal digital assistant, PDA, tablet, laptop computer, or desktop computer. The content can include a webpage, a video feed, a social sharing network or platform, etc. Other content can be included such as an image or a video of a user 2622, an emotion designation, 2626, a media presentation 2628, and so on. When an emotion 2626 is determined, a representation of that emotion 2624 can be determined. In embodiments, the graphical representation 2624 can include an emoji or an emoticon. The representation 2624 of the emotion can include an animated emoji, a cartoon, a GIF, etc., as outlined above. The representation 2624 can be displayed along with the other content displayed on the screen 2610. In embodiments, more than one representation can be displayed. The graphical representation can be displayed on or adjacent to the image 2622 of the user.

Figure 27:
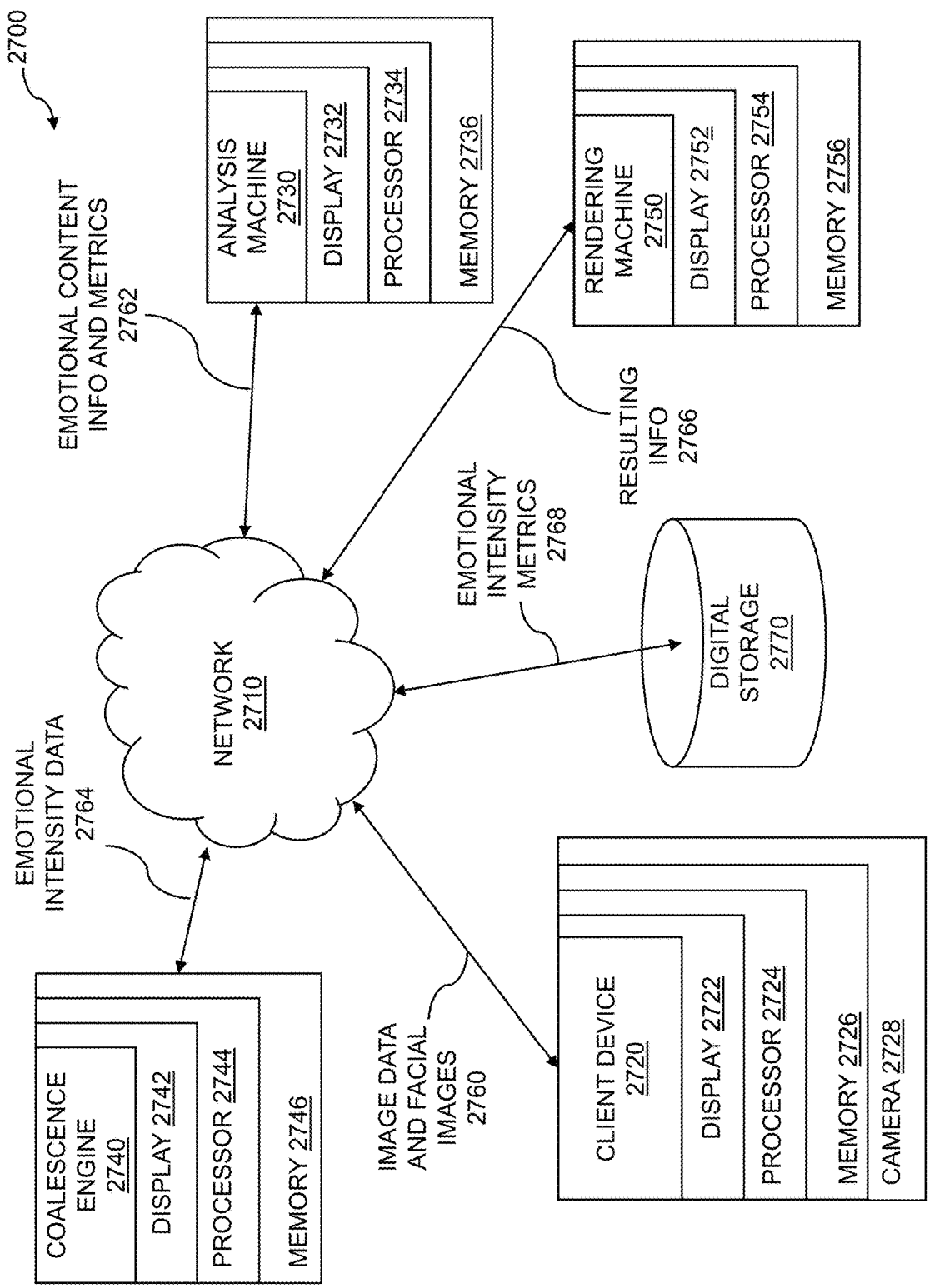
FIG. 27 is a diagram of a system for image analysis and representation for emotional metric threshold evaluation.

FIG. 27 is a diagram of a system for image analysis and representation for emotional metric threshold evaluation. Image data of a user interacting with a media presentation is collected at a client device, where the image data comprises facial images of the user. One or more processors are used to analyze the image data to extract emotional content of the facial images. One or more emotional intensity metrics are determined based on the emotional content. One or more emotional intensity metrics are stored into a digital storage component. The one or more emotional intensity metrics, obtained from the digital storage component, are coalesced into a summary emotional intensity metric. The summary emotional intensity metric is represented. The network 2710, such as the Internet, an intranet, or another wired, wireless, or hybrid computer network, can be used for communication among the various machines that comprise a system for image analysis. A client device 2720 has a memory 2726 which stores instructions and one or more processors 2724 attached to the memory 2726, wherein the one or more processors 2724 can execute instructions. The client device 2720 can also have an internet connection to carry mental state, audio, and facial images data 2760, and a display 2722 that can present various renderings to a user. The client device 2720 can collect mental state data from a plurality of people as they interact with a rendering. The client device 2720 can include a camera 2728. The camera 2728 can include a webcam, a video camera, a still camera, a thermal imager, a CCD device, a phone camera, a three-dimensional camera, a depth camera, a light field camera, a plenoptic camera, multiple webcams used to show different views of a person, or any other type of image capture technique that can allow captured data to be used in an electronic system. In some embodiments, there are multiple client devices 2720 that each collect mental state data including facial data from one person or a plurality of people as they interact with a rendering. The client device 2720 can communicate with an analysis machine 2730 and other machines over the network 2710, the Internet, some other computer network, or by another method suitable for communication between two computers. In some embodiments, the analysis machine 2730 functionality is embodied in the client device 2720.

A coalescence engine 2740 can have a network connection for emotional intensity data 2764, a memory 2746 which stores instructions, and one or more processors 2744 attached to the memory 2746, wherein the one or more processors 2744 can execute instructions. The coalescence engine 2740 can coalesce emotional intensity data and can generate a summary emotional intensity metric. The emotional intensity data can be determined for one or more individuals interacting with one or more client devices 2720. The coalescence engine 2740 can coalesce emotional intensity metrics, summary emotional intensity metrics, etc. In some embodiments, the coalescence engine 2740 renders content on a display 2742. The display 2742 can be any electronic display, including but not limited to, a computer display, a laptop screen, a net-book screen, a tablet computer screen, a smartphone display, a mobile device display, a remote with a display, a television, a projector, or the like.

An analysis machine 2730 can have a network connection for emotional content information and metrics 2762, a memory 2736 which stores instructions, and one or more processors 2734 attached to the memory 2736, wherein the one or more processors 2734 can execute instructions. The analysis server 2730 can receive emotional content information and metrics 2762 collected from one or more people as they interact with a rendering such as a media presentation from the client device 2720 and can analyze, aggregate, coalesce, etc., the mental state information on the plurality of people who interact with the rendering. In some embodiments, the analysis machine 2730 also allows a user to view and evaluate the emotional content information and metrics that are associated with the rendering on a display 2732. A rendering machine 2750 can have a memory 2756 which stores instructions, and one or more processors 2754 attached to the memory 2756, wherein the one or more processors 2754 can execute instructions. The rendering machine 2750 can use a network connection, Internet, or another computer communication technique, to send and receive resulting information 2766. The rendering machine 2750 can receive image data and facial images 2760, emotional intensity data 2764, resulting information 2766 such as emotional intensity metrics, coalesced emotional intensity metrics, etc., emotional content information and metrics 2762, etc. The data and information can be rendered on a display 2752. A digital storage component 2770 can have a network connection for emotional intensity metrics 2768. The digital storage component can storage image data and facial images, emotional intensity data, emotional content information and metrics. Representations of one or more summary emotional intensity metrics, and the like.

In embodiments, the system 2700 includes a computer program product embodied in a non-transitory computer readable medium for image analysis, the computer program product comprising code which causes one or more processors to perform operations of: collecting, at a client device, image data of a user interacting with a media presentation, wherein the image data comprises facial images of the user; analyzing, using one or more processors, the image data to extract emotional content of the facial images; determining one or more emotional intensity metrics based on the emotional content; storing the one or more emotional intensity metrics into a digital storage component; coalescing the one or more emotional intensity metrics, obtained from the storage component, into a summary emotional intensity metric; and representing the summary emotional intensity metric.

In other embodiments, the system 2700 includes a computer program product embodied in a non-transitory computer readable medium for image analysis comprising code which causes one or more processors to perform operations of: collecting, at a client device, image data of a user interacting with a media presentation, wherein the image data comprises facial images of the user; analyzing, using one or more processors, the image data to extract emotional content of the facial images; determining one or more emotional intensity metrics based on the emotional content; storing the one or more emotional intensity metrics into a digital storage component; detecting that a threshold value has been met by the one or more emotional intensity metrics; generating a graphical representation of a facial expression for the user based on the threshold value having been met; and attaching the graphical representation to a representation of the media presentation.

Each of the above methods may be executed on one or more processors on one or more computer systems. Embodiments may include various forms of distributed computing, client/server computing, and cloud based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for image analysis comprising:
    collecting, at a client device, image data of a user interacting with a media presentation, wherein the image data comprises facial images of the user;
    analyzing, using one or more processors, the image data to extract emotional content of the facial images;
    determining one or more emotional intensity metrics based on the emotional content; storing the one or more emotional intensity metrics into a digital storage component;
    detecting that a threshold value has been met by the one or more emotional intensity metrics, wherein the threshold value is based on evaluation of facial movements of the user;
    coalescing the one or more emotional intensity metrics, obtained from the digital storage component, into a summary emotional intensity metric;
    comparing the summary emotional intensity metric to an emotional intensity goal, wherein the emotional intensity goal includes increasing a daily percentage of a particular emotion; and
    representing the summary emotional intensity metric.
2. The method of claim 1 wherein the threshold value is based on evaluation of facial movements of a group of users.
3. The method of claim 1 further comprising generating a video, using the image data of the user, based on the threshold value having been met.
4. The method of claim 3 further comprising transmitting the video to a display device.
5. The method of claim 3 wherein the video includes image frames from before the threshold value was met.
6. The method of claim 1 wherein the representing includes displaying the summary emotional intensity metric or the one or more emotional intensity metrics.
7. The method of claim 1 further comprising displaying information on content of the media presentation.
8. The method of claim 1 further comprising augmenting the collecting image data with collecting audio data.
9. The method of claim 8 wherein the audio data includes speech.
10. The method of claim 1 further comprising selecting an image from the facial images, wherein the image that was selected is based on a highest intensity emotion.
11. The method of claim 1 further comprising capturing self-images of the user based on the one or more emotional intensity metrics.
12. The method of claim 11 further comprising displaying the self-images along with the summary emotional intensity metric.
13. The method of claim 1 wherein the coalescing further comprises counting occurrences of a specific emotion type within the emotional content.
14. A computer-implemented method for image analysis comprising:
    collecting, at a client device, image data of a user interacting with a media presentation, wherein the Image data comprises facial images of the user: analyzing, using one or more processors, the image data to extract emotional content of the facial images;
    determining one or more emotional intensity metrics based on the emotional content;
    storing the one or more emotional intensity metrics into a digital storage component;
    detecting that a threshold value has been met by the one or more emotional intensity metrics, wherein the threshold value is based on evaluation of facial movements of the user;
    comparing at least one of the one or more emotional intensity metrics to an emotional intensity goal, wherein the emotional intensity goal includes increasing a daily percentage of a particular emotion;
    generating a graphical representation of a facial expression for the user based on the threshold value having been met; and
    attaching the graphical representation to a representation of the media presentation.
15. The method of claim 14 wherein the graphical representation includes an emoji or an emoticon.
16. The method of claim 15 wherein the emoji includes an animated emoji.
17. The method of claim 14 wherein the threshold value is based on evaluation of facial movements of a group of users.
18. The method of claim 14 wherein the graphical representation comprises a video.
19. The method of claim 18 wherein the video includes image frames from before the threshold value was met.
20. A computer program product embodied in a non-transitory computer readable medium for image analysis, the computer program product comprising code which causes one or more processors to perform operations of:
    collecting, at a client device, image data of a user interacting with a media presentation, wherein the image data comprises facial images of the user;
    analyzing, using one or more processors, the image data to extract emotional content of the facial images;

determining one or more emotional intensity metrics based on the emotional content;

storing the one or more emotional intensity metrics into a digital storage component;

detecting that a threshold value has been met by the one or more emotional intensity metrics, wherein the threshold value is based on evaluation of facial movements of the user;

coalescing the one or more emotional intensity metrics, obtained from the storage component, into a summary emotional intensity metric;

comparing the summary emotional intensity metric to an emotional intensity goal, wherein the emotional intensity goal includes increasing a daily percentage of a particular emotion; and representing the summary emotional intensity metric.

21. The method of claim 1 wherein the increasing a daily percentage of a particular emotion is for a current time period compared to a summary emotional intensity metric generated based on a previous time period.

22. The method of claim 21 wherein the particular emotion is happiness and the current time period is a day.

23. The method of claim 1 further comprising displaying a dashboard providing simultaneous indications of progress toward at least two emotional intensity goals for a current time period.

24. The method of claim 23 further comprising providing suggestions for activities selected to help the user improve their mood.

* * * * *